US 6,555,698 B1

(12) United States Patent
Edwards et al.

(10) Patent No.: US 6,555,698 B1
(45) Date of Patent: Apr. 29, 2003

(54) CHEMILUMINESCENT SUBSTRATES FOR NEURAMINIDASE, ASSAYS FOR DETECTION OF NEURAMINIDASE AND KITS THEREFOR

(75) Inventors: Brooks Edwards, Cambridge; Irena Bronstein, Newton; Rouh-Rong Juo, Allston, all of MA (US)

(73) Assignee: Tropix, Inc., Bedford, MA (US)

( * ) Notice: Subject to any disclaimer, the term of this patent is extended or adjusted under 35 U.S.C. 154(b) by 0 days.

(21) Appl. No.: 09/441,064

(22) Filed: Nov. 16, 1999

Related U.S. Application Data

(60) Provisional application No. 60/108,703, filed on Nov. 17, 1998.

(51) Int. Cl.$^7$ .................. C07D 305/00; C07D 321/00; C12N 9/24; C12Q 1/70
(52) U.S. Cl. ............... 549/510; 549/200; 435/200; 435/5
(58) Field of Search ................. 435/200, 201, 435/5; 549/510, 200

(56) References Cited

U.S. PATENT DOCUMENTS

| | | | | |
|---|---|---|---|---|
| 4,952,707 A | * | 8/1990 | Edwards et al. ............ | 549/221 |
| 5,112,960 A | * | 5/1992 | Bronstein et al. ........... | 536/18.1 |
| 5,616,729 A | * | 4/1997 | Schaap et al. .............. | 549/223 |

FOREIGN PATENT DOCUMENTS

WO      92/07572      5/1992

OTHER PUBLICATIONS

Shimasaki et al., U.S. Patent Application of Unknown Serial Number and filing date claiming priority to U.S. Provisional Application Ser. No. 60/129,602, filed Apr. 16, 1999, entitled "Viral Detection Method Using Viral Encoded Enzymes and Chemiluminescent Substrates".

Henricks et al., "Partial Removal of Sialic Acid Enhances Phagocytosis and the Generation of Superoxide and Chemiluminescence by Polymorphonuclear Leukocytes," The Journal of Immunology, Aug. 1982, Vol. 129, No. 2, pp. 745–750, especially p. 745.

\* cited by examiner

Primary Examiner—Ralph Gitomer
Assistant Examiner—Mahreen Chaudhry
(74) Attorney, Agent, or Firm—Piper Rudnick LLP; Steven B. Kelber

(57) ABSTRACT

The present invention discloses chemiluminescent 1,2-dioxetane substrates capable of reacting with a neuraminidase to release optically detectable energy. These 1,2-dioxetanes have the general formula:

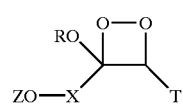

I wherein Z is

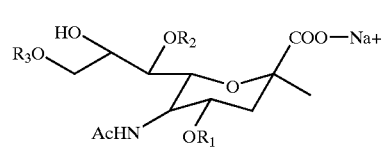

II and the variables are selected so as to induce decomposition of said dioxetane accompanied by chemiluminescence where Z is cleaved by neuraminidase present.

21 Claims, 24 Drawing Sheets

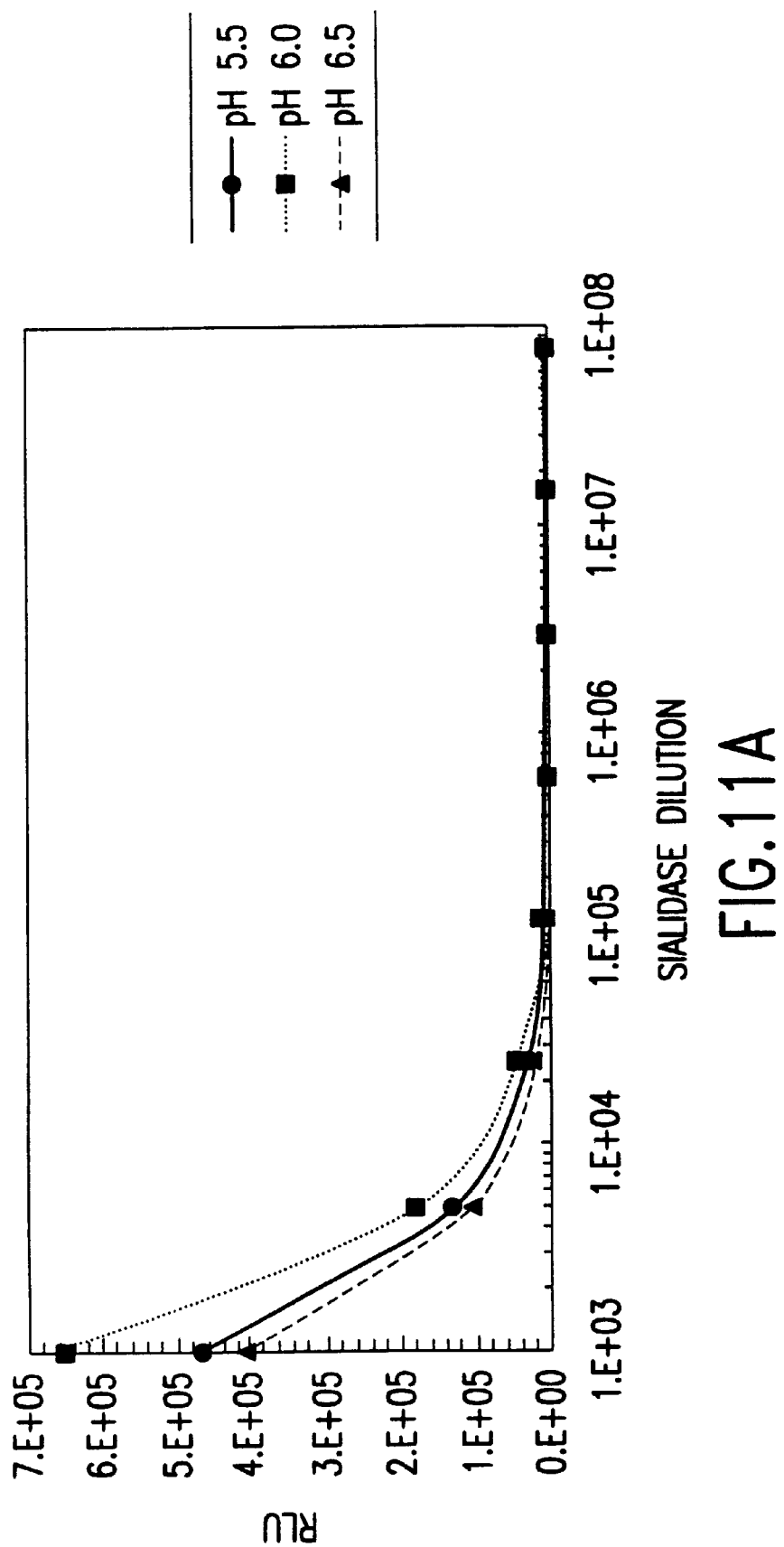

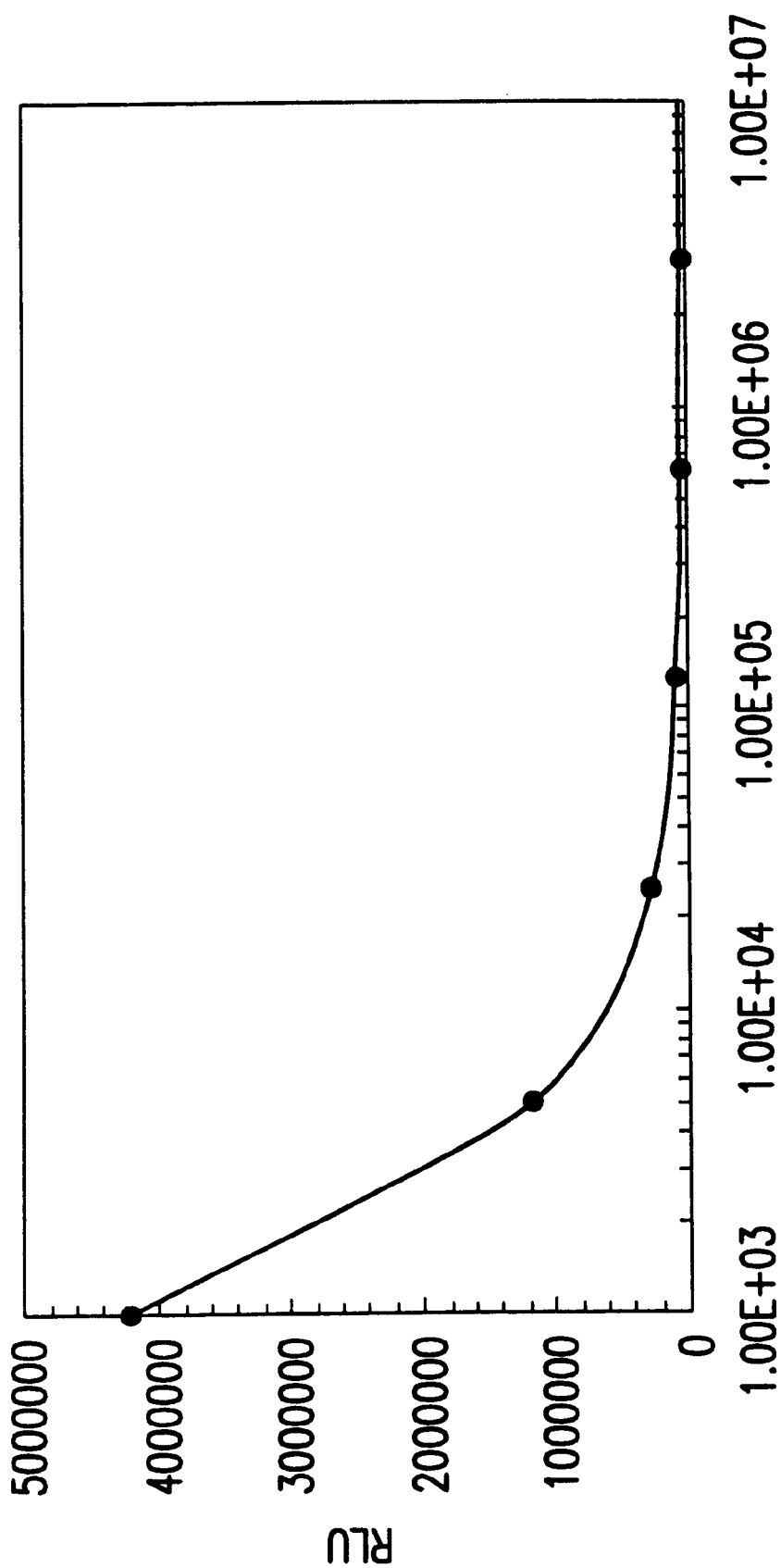

CHEMILUMINESCENT SUBSTRATES FOR NEURAMINIDASE, ASSAYS FOR DETECTION OF NEURAMINIDASE AND KITS THEREFOR

This application is a regular National application claiming priority from Provisional Application, U.S. application Ser. No. 60/108,703 filed Nov. 17, 1998. The entirety of that provisional application is incorporated herein by reference.

BACKGROUND OF THE INVENTION

1. Field of the Invention

This invention pertains to a novel 1,2-dioxetane substrate for use in a chemiluminescent assay for the detection of neuraminidase. This invention takes advantage of the high sensitivity of chemiluminescent 1,2-dioxetane reagents to overcome sensitivity problems encountered in the prior art. Additionally, this invention pertains to methods and kits employing such dioxetanes.

2. Background of the Prior Art

A wide variety of diseases and infections are caused by viruses. Of all of these known diseases and infections, respiratory infections such as those caused by influenza viruses are the most common. Acute respiratory infections can be fatal, especially in elderly patients. Consequently, the development of assays for the detection of viruses and viral infections has become increasingly important.

In general, influenza viruses express surface glycoproteins that have neuraminidase activity. The enzyme neuraminidase, also known as sialidase, is a well-characterized hydrolytic enzyme that has an optimum pH at 5.5 and hydrolyzes substrates that contain 2-ketosidically linked n-acetylneuraminic acids (Neu5ac, also known as sialic acid). This low optimum pH (5.5) for the neuraminidase enzyme makes it difficult to obtain an assay for neuraminidase that has adequate sensitivity.

The detection of neuraminidase is important because neuraminidase is implicated in a variety of biological events. For example, a deficiency in this enzyme leads to sialidosis, an autosomal recessive trait. Additionally, it is known that the release of neuraminidase mediates the penetration of cells by influenza viruses.

Because the early detection of influenza viruses allows for a more effective treatment, it is desirable to have a highly sensitive assay for the early detection of influenza viruses. However, it is very difficult to detect influenza viruses at an early stage using conventional technology because the clinical samples obtained often do not have a sufficient amount of neuraminidase present to be able to be detected by current technology.

A chromogenic/fluorogenic neuraminidase substrate has been developed and is reported in U.S. Pat. No. 5,719,020, Liav, et al. The same is incorporated herein by reference. While the substrate and assay provided in this reference offers some enhancement of specificity and reliability in detection, in fact, the use of chromogenic or fluorogenic reporter molecules suffers from a variety of drawbacks in detection mechanisms, note, for instance, the detailed collection and assessment steps necessary in the assay described in U.S. Pat. No. 5,719,020. A simpler, more reliable, quantifiable detection system is desirable. The problems with specificity for this specific assay are also discussed in Reinhard et al., Biol. Chem., Volume 373, pages 63–68 (1992).

Chemiluminescent substrates release light for a positive indication of the presence of a particular substance in a sample. Chemiluminescent assays which utilize these chemiluminescent substrates are attractive assays because they avoid the need for special procedures for using and discarding radioactive materials. Additionally, chemiluminescent assays typically do not require complicated or involved apparatus for detection of the assayed substance. Further, chemiluminescent assays may be enhanced by water soluble enhancers to enhance the total luminosity. Typical enhancers are set forth in U.S. Pat. No. 5,145,772, incorporated herein by reference.

The assignee of this application, Tropix, Inc., has developed a wide array of chemiluminescent enzyme substrates for use in detection assays, many of which utilize 1,2-dioxetanes. Representative patents addressing these chemiluminescent enzyme substrates include U.S. Pat. Nos. 4,931,223; 4,931,569; 4,952,707; 4,956,477; 4,978,614; 5,032,381; to 5,112,960; 5,145,772; 5,220,005; 5,225,584; 5,326,882; 5,330,900; 5,336,596; 5,869,699; 5,538,847; and 5,871,938, all of which are incorporated herein by reference.

The above-referenced patents address 1,2-dioxetanes which are stabilized by a polycyclic group bonded to one of the carbons in the four membered ring portion of the dioxetane by a Spiro linkage. An electron-rich moiety, typically an aryl group, a phenyl, or a naphthyl group, is bonded to the remaining carbon of the dioxetane ring. Attached to this moiety is an enzyme-cleavable group. When this group is cleaved, an anion is generated which decomposes, causing the dioxetane to release light. In addition, the carbon that bears the above-identified electron-rich moiety may also bear an alkoxy or other electron-active group.

As disclosed in U.S. Pat. No. 5,112,960, an enzyme-triggerable dioxetane such as 3-(4-methoxy-spiro[1,2-dioxetane-3,2'-tricyclo[3.3.1.1$^{3,7}$]decan]-4-yl-phenyl phosphate and its salts (AMPPD®) is a highly effective reporter molecule. Superior performance can be obtained by selective substitution on the polycyclic group. For example, substitution with an electron-active species, such as chlorine, has been shown to dramatically improve reaction speed and signal-to-noise ratio (S/N). The chlorine-substituted counterpart of AMPPD®, CSPD®, has been widely commercialized by Tropix, Inc. "Third-generation" dioxetane compounds of similar structure, wherein the phenyl or naphthyl moiety also bears an electron-active substituent, such as chlorine, offer further improvements in performance. These "third generation" dioxetanes have also been commercialized by Tropix, Inc. The phosphate moieties are available under the trademarks CDP® and CDP-STAR®. These reporter molecules, which are chemiluminescent in nature, are referred to as enzyme-triggerable dioxetanes. To date, alkaline phosphatase has been the dominant enzyme of interest as a triggering agent.

Although much is known about chemiluminescent assays generally, the existing literature does not describe a triggerable dioxetane which is specific for the neuraminidase enzyme. Furthermore, the existing literature does not disclose a chemiluminescent detection assay, or a substrate for use in such an assay, for the sensitive detection of neuraminidase. Accordingly, a need exists for a 1,2-dioxetane compound which can be used to detect the presence of neuraminidase. Thus, it remains a goal of one of ordinary skill in the art to find an assay to detect the presence of the neuraminidase enzyme which is highly sensitive and employs reagents which can be obtained through simplified procedures.

SUMMARY OF THE INVENTION

The above objects, and other discussed in more detail below, are met by a chemiluminescent assay which relies on chemiluminescent 1,2-dioxetanes. Other dioxetanes, developed by the assignee here, Tropix, Inc., are the subject of a wide variety of United States patents. The 1,2-dioxetane substrates useful in the present invention are generally represented by the following formula:

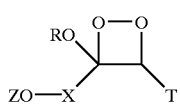

I wherein T is a substituted or unsubstituted polycycloalkyl group bonded to the 4-membered ring portion of said dioxetane by a spiro linkage, said substituents being independently selected from the group consisting of a hydroxyl group, fluorine, chlorine, an unsubstituted straight or branched chain alkyl group of 1–6 carbon atoms, a 1–6 carbon alkyl group mono-, di- or tri- substituted with a hydroxy or 1–3 halogen atoms, a phenyl group, a cyano group and an amide group;

wherein X is selected from the group consisting of phenyl, naphthyl and other heteroaryls, and wherein X bears 1–3 electron active substituents, each electron active substituent being independently selected from the group consisting of halogen (particularly F and Cl), alkoxy, aryloxy, trialkylammonium, alkylamido, arylamido, arylcarbamoyl, alkylcarbamoyl, cyano, nitro, ester, alkylsulfonamido, arylsulfonamido, triphorylmethyl, aryl, alkyl, trialkyl, triarylsilyl, alkylarylsilyl, alkylamidosulfonyl, arylamidosulfonyl, alkylsulfonyl, arylsulfonyl, alkylthioether and arylthioether, and wherein, each alkyl or aryl moiety comprises 1–12 carbon atoms;

wherein Z is an enzymatically cleavable group of formula II:

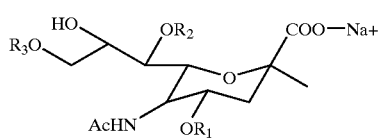

II and $R_1$–$R_3$ are hydrogen or alkyl groups (straight chain or branched) of 1–4 carbon atoms;

and wherein R is an alkyl, aryl, aralkyl or cycloalkyl of 1–20 carbon atoms, which may contain 1–2 hetero atoms selected from the group consisting of phosphorus, nitrogen, sulfur and oxygen; and wherein R can bear at least one halogen substituent.

It is another object of this invention to provide diagnostic kits and methods for detecting neuraminidase employing such substrates.

BRIEF DESCRIPTION OF THE DRAWINGS

FIG. 11A is a graph showing chemiluminescence (RLU) as a function of sialidase dilution for a substrate according to the invention in a 0.05 M sodium acetate/0.1M NaCl buffer.

FIG. 12A is a graph showing chemiluminescence (RLU) as a function of sialidase dilution using a methylumbelliferyl-N-acetylneuraminic acid salt fluorescent substrate in a 0.05 M sodium acetate/0.1M NaCl buffer.

DETAILED DESCRIPTION OF THE INVENTION

The structure, synthesis, and use of preferred embodiments of the present invention will now be described.

Structure

The present invention employs 1,2-dioxetanes of the general formula:

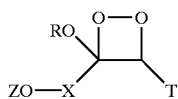
I which is capable of producing light energy when decomposed;

wherein T is a substituted or unsubstituted polycycloalkyl group bonded to the 4-membered ring portion of said dioxetane by a spiro linkage, said substituents being independently selected from the group consisting of a hydroxyl group, fluorine, chlorine, an unsubstituted straight or branched chain alkyl group of 1–6 carbon atoms, a 1–6 carbon alkyl group mono-, di- or tri-substituted with a hydroxy or 1–3 halogen atoms, a phenyl group, a cyano group and an amide group;

wherein X is selected from the group consisting of phenyl, naphthyl and other heteroaryls, and wherein X bears 1–3 electron active substituents, each electron active substituent being independently selected from the group consisting of halogen (particularly F and Cl), alkoxy, aryloxy, trialkylammonium, alkylamido, arylamido, arylcarbamoyl, alkylcarbamoyl, cyano, nitro, ester, alkylsulfonamido, arylsulfonamido, triphorylmethyl, aryl, alkyl, trialkyl, triarylsilyl, alkylarylsilyl, alkylamidosulfonyl, arylamidosulfonyl, alkylsulfonyl, arylsulfonyl, alkylthioether and arylthioether, and wherein, each alkyl or aryl moiety comprises 1–12 carbon atoms;

wherein Z is an enzymatically cleavable group of formula II:

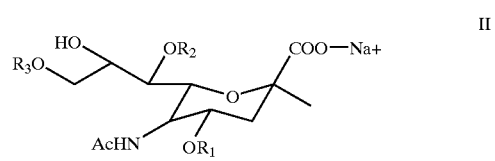
II and $R_1$–$R_3$ are hydrogen or alkyl groups (straight chain or branched) or 1–4 carbon atoms; and wherein R is an alkyl, aryl, aralkyl or cycloalkyl of 1–20 carbon atoms, which may contain 1–2 hetero atoms selected from the group consisting of phosphorus, nitrogen, sulfur and oxygen; and wherein R can bear at least one halogen substituent.

Any one of X, T or R, most preferably R can bear one or more groups which enhance the solubility of the dioxetane reagent in aqueous preparations. Typical moieties of this type include sulfonyl groups, carboxylic acid moieties such as COOH, fluorine or halogen based groups, including trifluoro substituent and the like. In some preferred embodiments, two solubility enhancing groups may be present.

The 1,2-dioxetanes according to the present invention are unusual in that the 1,2-dioxetane aglycone is constructed such that the pKa of the leaving group upon enzyme cleavage may be low enough so that light may be produced concomitantly with enzyme action. The neuraminidase enzyme has pH optimum ranges which vary from 5.5 to 7.8, depending on the type and medium. The thermal stability of the neuraminidase substrate of the present invention is greater at a higher pH.

Figure 1:
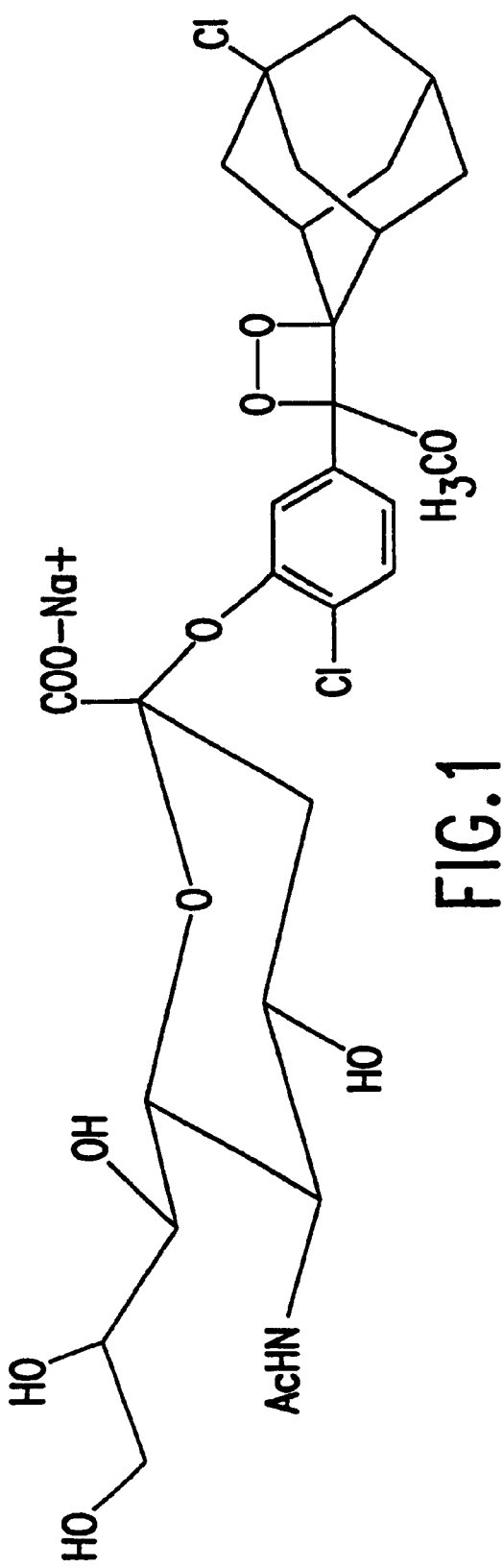
FIG. 1 is a neuraminidase substrate.
Figure 3:
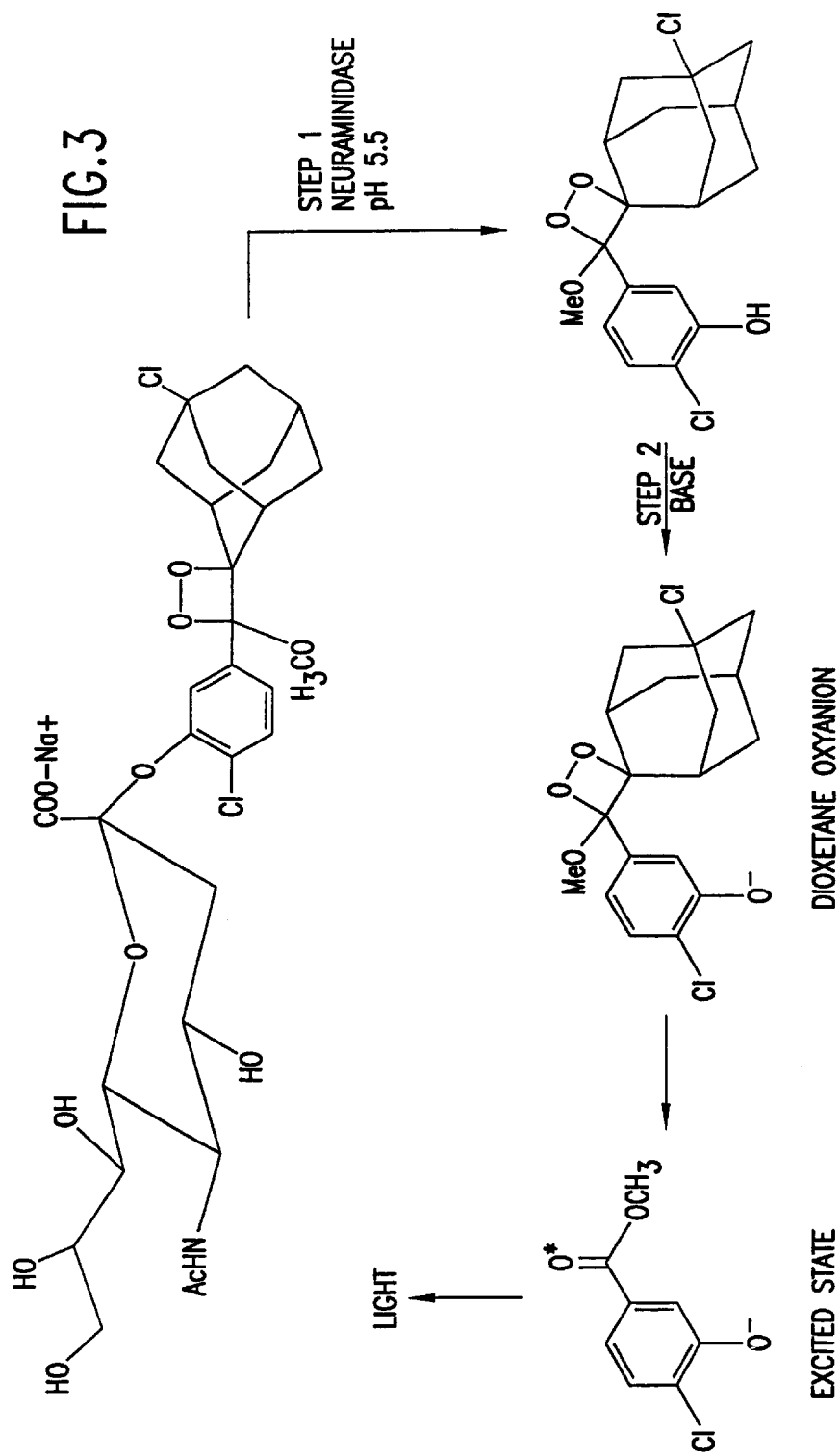
FIG. 3 is a flowchart illustration of the mechanism for a neuraminidase-induced light emission.

Specifically, in circumstances where the aryl moiety X bears electron active substituents, such as a chlorine moiety in the para or meta position, as reflected in FIG. 1, the pKa of the leaving group upon cleavage is sufficient such that at the optimum pH of the neuraminidase enzyme of 5.5–7.8, sufficient light is produced to achieve a sustained glow characteristic of dioxetane chemiluminescent emission, which sustained glow is desirable for high speed throughput and automation. In this case, a one step assay (contact with the enzyme) is employed. It may frequently be desirable, however, to control the speed and performance of the assay by using a substrate which requires the addition of base to elevate the pH to achieve the sustained glow emission. In this situation, the aryl ring (in the case of FIG. 1, a phenyl moiety) does not bear additional electron active substituents, other than the oxygen linkage. The resulting oxyanion gives a sustained glow at a pH above the active range of the enzyme, e.g., above about 8.5, and thus, detection can be separated from reaction and conditions of the assay can be controlled. Thus, the invention provides for either a one or two step assay, depending on the users preference. A two step assay is illustrated in FIG. 3, using the molecule of FIG. 1. The same assay could be performed without the addition of base, and a glow of lower intensity, but nonetheless sustained emission, would be detected, depending on the actual pH employed.

The substrates provided by the present invention are capable of providing a continuous chemiluminescence-based assay at a pH which is in concert with both enzyme action and the triggering of the fragment to allow either a one step or two step assay. This flexibility offers significant advantages and format compatibility.

This invention lends itself to the use of enhancer detection of chemiluminescence. The enhancers are based, in general, on polymeric onium salts, particularly quaternary salts based on phosphonium, sulfonium and, preferably, ammonium moieties. The polymers have the general formula III shown below:

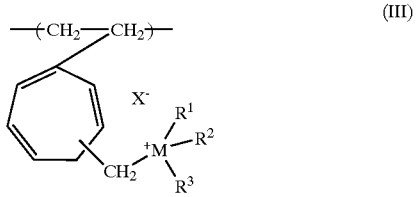

(III)

In this formula each of $R^1$, $R^2$ and $R^3$ can be a straight or branched chain unsubstituted alkyl group having from 1 to 20 carbon atoms, inclusive, e.g., methyl, ethyl, n-butyl, t-butyl, hexyl, or the like; a straight or branched chain alkyl group having from 1 to 20 carbon atoms, inclusive, substituted with one or more hydroxy, alkoxy, e.g., methoxy, ethoxy, benzyloxy or polyoxethylethoxy, aryloxy, e.g., phenoxy, amino or substituted amino, e.g., methylamino, amido, e.g., acetamido or ureido, e.g., phenyl ureido; or fluoroalkane or fluoroaryl, e.g., heptafluorobutyl groups, an unsubstituted monocycloalkyl group having from 3 to 12 carbon ring carbon atoms, inclusive, e.g., cyclohexyl or cyclooctyl, a substituted monocycloalkyl group having from 3 to 12 ring carbon atoms, inclusive, substituted with one or more alkyl, alkoxy or fused benzo groups, e.g., methoxycyclohexyl or 1,2,3,4-tetrahydronaphthyl, a polycycloalkyl group having from 2 or more fused rings, each having from 5 to 12 carbon atoms, inclusive, unsubstituted or substituted with one or more alkyl, alkoxy or aryl groups, e.g., 1-adamantyl or 3-phenyl-1-adamantyl, an aryl, alkaryl or aralkyl group having at least one ring and from 6 to 20 carbon atoms in total, unsubstituted or substituted with one or more alkyl, aryl, fluorine or hydroxy groups, e.g., phenyl, naphthyl, pentafluorophenyl, ethylphenyl, benzyl, hydroxybenzyl, phenylbenzyl or dehydroabietyl; at least two of $R^1$, $R^2$ and $R^3$, together with the quaternary nitrogen atom to which they are bonded, can form a saturated or unsaturated, unsubstituted or substituted nitrogen-containing, nitrogen and oxygen-containing or nitrogen and sulfur-containing ring having from 3 to 5 carbon atoms, inclusive, and 1 to 3 heteroatoms, inclusive, and which may be benzoannulated, e.g., 1-pyridinium, 1-(3-alkyl or aralkyl)imidazolium, morpholino, alkyl morpholinium, alkylpiperidinium, acylpiperidinium, piperidino or acylpiperidino, benzoxazolium, benzthiazolium or benzamidazolium.

The symbol $X^-$ represents a counterion which can include, alone or in combination, moieties such as halide, i.e., fluoride, chloride, bromide or iodide, sulfate, alkylsulfonate, e.g., methylsulfonate, arylsulfonate, e.g., p-toluenesulfonate, substituted arylsulfonate, e.g., anilinonaphthylenesulfonate (various isomers), diphenylanthracenesulfonate, perchlorate, alkanoate, e.g., acetate, arylcarboxylate, e.g., fluorescein or fluorescein derivatives, benzoheterocyclic arylcarboxylate, e.g., 7-diethylamino-4-cyanocoumarin-3-carboxylate, organicdianions such as p-terephthalate may also be represented by $X^-$.

The symbol n represents a number such that the molecular weight of such poly(vinylbenzyl quaternary ammonium salts) will range from about 800 to about 200,000 (weight average), and preferably from about 20,000 to about 70,000, as determined by intrinsic viscosity or LALLS techniques.

Methods for the preparation of these polymers, related copolymers and the related starting materials where M is nitrogen are disclosed in G. D. Jones et al, Journal of Polymer Science, 25, 201, 1958; in U.S. Pat. Nos. 2,780,604; 3,178,396; 3,770,439; 4,308,335; 4,340,522; 4,424,326 and German Offenlegunsschrift 2,447,611.

The symbol M may also represent phosphorous or sulfur whereupon the corresponding sulfonium or phosphonium polymers have been described in the prior art: U.S. Pat. Nos. 3,236,820 and 3,065,272.

Methods of preparation of the two polymers of this invention are set forth in the referenced U.S. patents, and do not constitute any aspect of this invention, per se.

Copolymers containing 2 or more different pendant onium groups may also be utilized in the invention described herein:

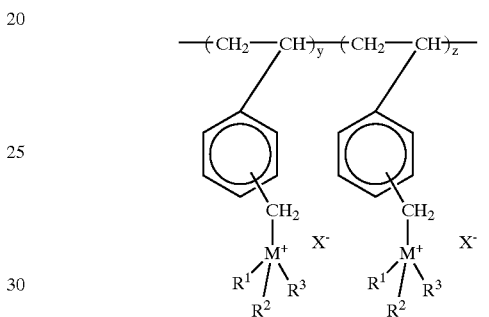

The symbols $X^-$, M, $R^1$, $R^2$, $R^3$ are as described above. The symbols y and z represent the mole fraction of the individual monomers comprising the copolymer. The symbols y and z may thus individually vary from 0.01 to 0.99, with the sum always equaling one.

As preferred moieties, M is N, and $R^1$–$R^3$ are individually, independently, cycloalkyl, polycycloalkyl (e.g. adamantane), aralkyl or aryl, having 1 to 20 carbon atoms, unsubstituted or further substituted with hydroxyl, amino, amido, ureido groups, or combine to form via a spiro linkage to the M atom a heterocyclic (aromatic, aliphatic or mixed, optionally including other N, S or O hetero atoms) onium moiety.

X is preferably selected to improve solubility and to change ionic strength as desired, and is preferably a halogen, a sulfate, or a sulfonate. In copolymers, each of $R^1$–$R^3$ may be the same as or different from the corresponding $R^1$–$R^3$. Examples of preferred polymers include the following:

- polyvinylbenzylphenylureidoethyldimethyl ammoniumchloride (PUDMQ);
- polyvinylbenzyldimethyl hydroxyethylammonium chloride (DMEQ);
- polyvinylbenzylbenzoylaminoethyldimethylammonium chloride (BAEDMQ);
- polyvinylbenzylbenzyldimethyl ammonium chloride (BDMQ);
- polyvinylbenzyltributyl ammonium chloride (TBQ);
- copolyvinylbenzyltrihexylammoniumchloridepolyvinylbenzyltributyl ammonium chloride (THQ-TBQ); and
- copolyvinylbenzylbenzyldimethylammonium chloridepolyvinyl aminoethyldimethylammonium chloride (BDMQ-AEDMQ).

These vinylbenzyl quaternary ammonium salt polymers can be prepared by free radical polymerization of the appropriate precursor monomers or by exhaustive alkylation of the corresponding tertiary amines with polyvinylbenzyl chloride, or copolymers containing a pendant benzyl chloride function. This same approach can be taken using other polymeric alkylating agents such as chloromethylated polyphenylene oxide or polyepichlorohydrin. The same polymeric alkylating agents can be used as initiators of oxazoline ring-opening polymerization, which, after hydrolysis, yields polyethyleneimine graft copolymers. Such copolymers can then be quaternized, preferably with aralkyl groups, to give the final polymer. These polymers are described, in detail, as membranes in U.S. Pat. No. 5,593,828, incorporated herein by reference. In the alternative, the dicationic enhancer of U.S. Pat. No. 5,650,099, incorporated herein by reference, can be used.

Synthesis of Dioxetane Neuraminidase Substrates

Figure 2A:
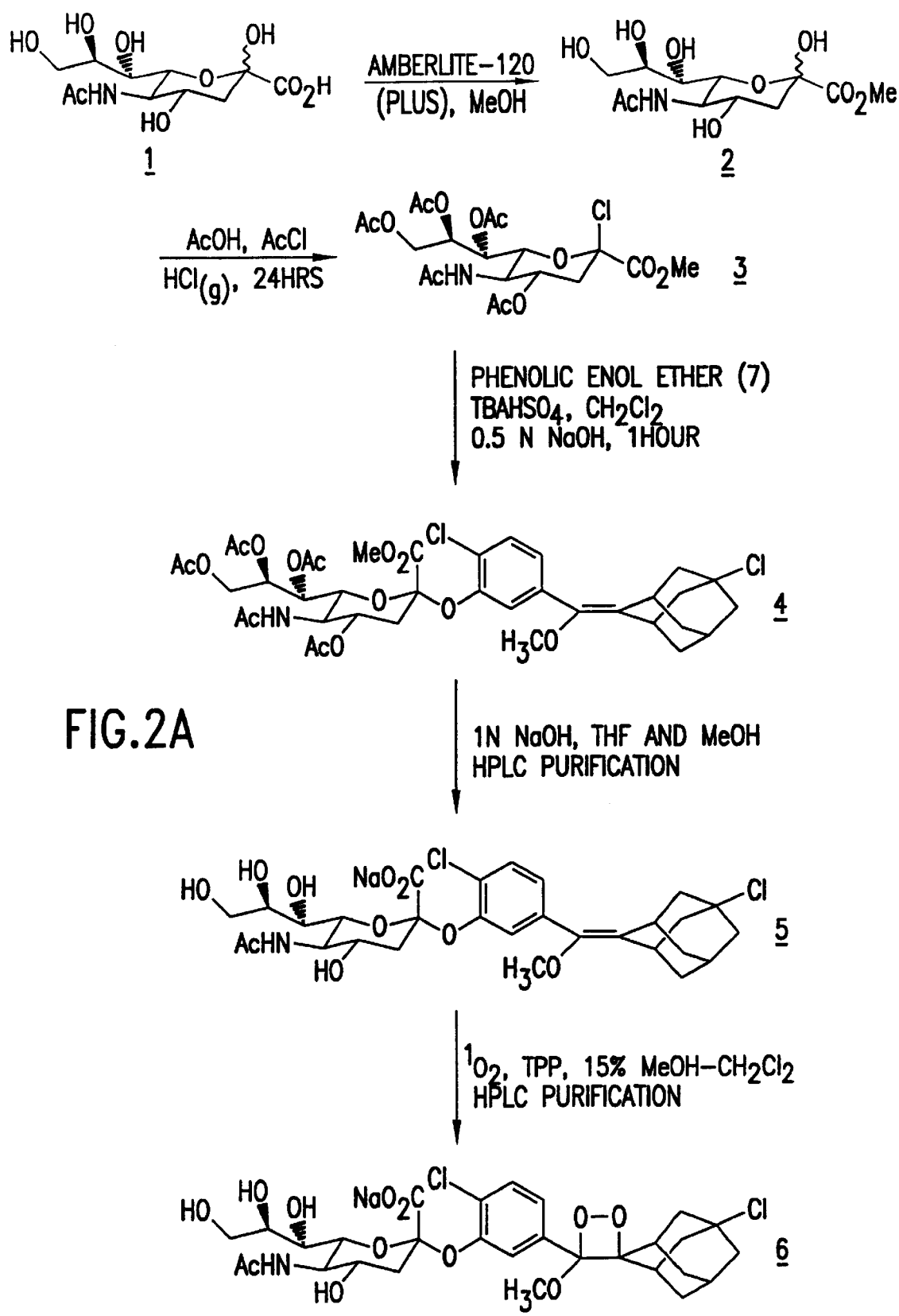
FIG. 2 is a flowchart illustration of a synthesis of a neuraminidase substrate.
Figure 2B:
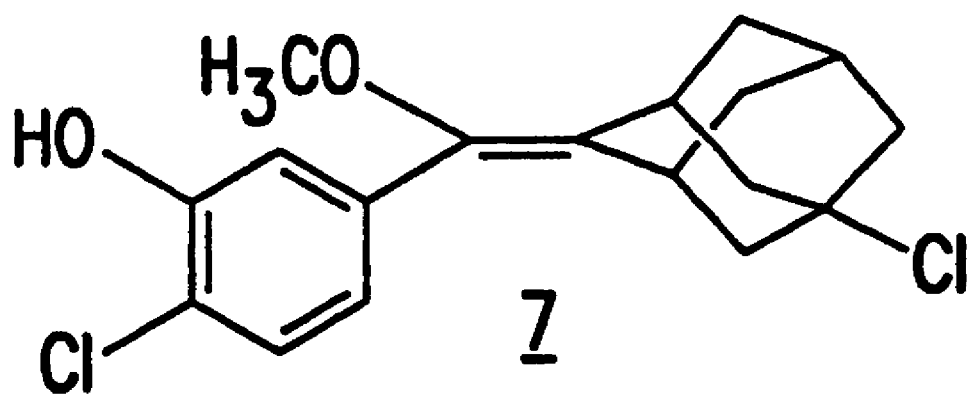
Figure 2B:
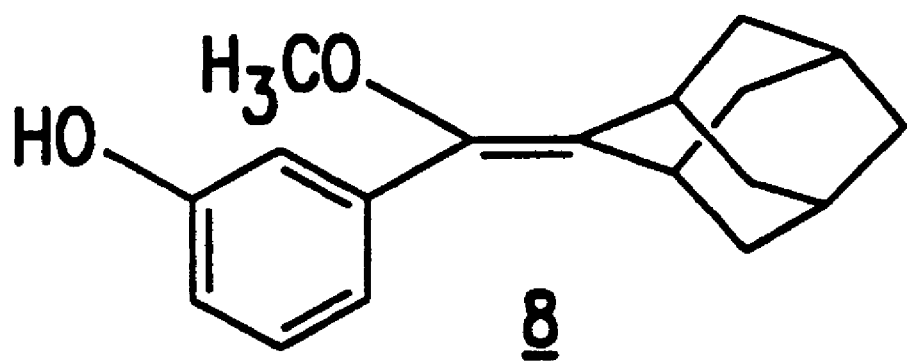

The following example is a representative synthesis of a 1,2-dioxetane as shown in FIG. 2 and should not limit the scope of the claims.

Methyl (5-acetamido-4,7,8,9-tetra-O-acetyl-3,5-dideoxy-D-glycero-β-D-galacto-nonulopyranosyl chloride)onate (compound 3 in FIG. 2)

Methyl (5-acetamido-4,7,8,9-tetra-O-acetyl-3,5-dideoxy-D-glycero-β-D-galacto-nonulopyranosyl chloride)onate was prepared in two steps from the commercially available N-acetylneuraminic acid (compound 1 in FIG. 2) according to the procedure set forth in Kuhn, R., Lutz, P. and McDonald, D. C., Chem. Ber., 99 (1966) 611–617. The crude methyl (5-acetamido-4,7,8,9-tetra-O-acetyl-3,5-dideoxy-D-glycero-β-D-galacto-nonulopyranosyl chloride)onate obtained was purified by a silica gel plug and eluted with 200 ml of 80–90% EtOAc in hexanes. After concentrating the filtrate, 1.24 g (2.43 mmole) of methyl (5-acetamido-4,7,8,9-tetra-O-acetyl-3,5-dideoxy-D-glycero-β-D-galacto-nonulopyranosyl chloride)onate was obtained as an off-white powder. This product was then immediately used in the following coupling reaction.

Methyl (2-chloro-5-(methoxy-5-chlorotricyclo[3.3.1.1$^{3,7}$]dec-2-ylidenemethyl)phenl 5-acetamido-4,7,8,9-tetra-O-acetyl-3,5-dideoxy-α-D-glycero-D-zalacto-2-nonulopyranosid)onate (compound 4 in FIG. 2)

2-Chloro-5-(methoxy-5-chlorotricyclo[3.3.1.1$^{3,7}$]dec-2-ylidenemethyl)phenol (1.65 g, 4.86 mmole) and the phase transfer catalyst tetrabutylammonium hydrogensulfate (0.83 g, 2.43 mmole) were placed in a 100 ml round-bottomed flask and treated with 12.5 ml of $CH_2Cl_2$ and 17.5 ml of 0.5 N NaOH at room temperature. The resulting two-phase mixture was added to a solution of the product set forth above (1.24 g 2.43 mmole) of methyl (5-acetamido-4,7,8,9-tetra-O-acetyl-3,5-dideoxy-D-glycero-β-D-galacto-nonulopyranosyl chloride)onate) in 5 ml of $CH_2Cl_2$.

After an hour of vigorous stirring, the reaction mixture was diluted with $CH_2Cl_2$ and poured into a separatory funnel containing a saturated sodium bicarbonate solution. After the organic layer was separated, the aqueous layer was extracted two additional times with $CH_2Cl_2$. The combined organic layer was then washed with $H_2O$ and dried over anhydrous $Na_2SO_4$. TLC (80% EtOAc in hexanes) showed the coupling product methyl (2-chloro-5-(methoxy-5-chlorotricyclo[3.3.1.1$^{3,7}$]dec-2-ylidenemethyl)phenyl 5-acetamido-4,7,8,9-tetra-O-acetyl-3,5-dideoxy-α-D-glycero-D-galacto-2-nonulopyranosid)onate at Rf=0.48 with faint shadows above and below. The organic solution was then treated with 10 drops of $ET_3N$ and concentrated.

Next, the crude product was purified by silica gel chromatography and eluted with 20% EtOAc in hexanes to recover the unreacted enol ether phenol (compound 7 in FIG. 2), followed by 80–90% EtOAc in hexanes, thereby affording 1.242 g (62.9%) of methyl (2-chloro-5-(methoxy-5-chlorotricyclo[3.3.1.1$^{3,7}$]dec-2-ylidenemethyl)phenyl 5-acetamido-4,7,8,9-tetra-O-acetyl-3,5-dideoxy-α-D-glycero-D-galacto-2-nonulopyranosid)onate as a light yellow, crispy foam.

IR(CHCl$_3$ cm$^{-1}$): 3432, 3040, 2936, 1750, 1688, 1372, 1235 and 1040. The $^1$H NMR (CDCl$_3$) spectrum was complicated, but it still could reveal that the sample actually was a mixture of about 4:3:1 of the desired product (compound 4) and glycal from the dehydrochlorination of the chloride (compound 3).

A clean sample was obtained by removing the O-acetyl groups with NaOMe in MeOH followed by reacylation with acetic anhydride in pyridine to remove the glycal. The resulting $^1$H NMR spectrum clearly showed that methyl (2-chloro-5-(methoxy-5-chlorotricyclo[3.3.1.1$^{3,7}$]dec-2-ylidenemethyl)phenyl 5-acetamido-4,7,8,9-tetra-O-acetyl-3,5-dideoxy-α-D-glycero-D-galacto-2-nonulopyranosid)onate existed as a 1:1 mixture of two isomers, based on the equal splitting of the methyl ester and O- and N-acetyl methyl signals. The presence of two triplets at 2.82 ppm and 2.86 ppm for H-3e of the neuraminic acid ring indicated that both of the isomers were α-pyranosides.

$^1$H NMR (CDCl$_3$): δ 7.35 (d, J=8.2 Hz, 1H), 7.21 (m, 1H), 6.99 (m, 1H), 5.25–5.34 (m, 3H), 4.98–5.10 (m, 1H), 4.14–4.31 (m, 3H), 4.03 (m, 1H), 3.75 and 3.747 (2s. 3H, Me ester), 3.43 (broad s, 1 H), 3.30 (s, 3H, OMe), 2.86 and 2.82 (2t, J=4.3 Hz, 1H), 2.13, 2.12, 2.10 and 2.07 (4s, 6H), 2.04 (s, 3H), 2.03 (s, 3H) and 1.91 (s, 3H).

The same phase-transfer coupling reaction was performed on 3-(methoxytricyclo[3.3.1.1$^{3,7}$]dec-2-ylidenemethyl) phenol (compound 8 in FIG. 2) to yield the corresponding coupled product.

IR (CHCl$_3$,cm$^1$): 3440, 3018, 2920, 2860, 1795, 1690, 1375, 1238, 1138, 1045; $^1$H NMR (CDCl$_3$): δ 7.26 (t, J=7.9 Hz), 7.04–7.10 (m, 2H), 6.97 (m, 1H), 5.27–5.37 (m, 4H), 4.97 (m, 1H) 3.68 (s, 3H, Me ester), 3.28 (s, 3H, OMe), 3.24 (broad s, 1H), 2.72 (dd, J=12.9, 4.6 Hz, 1H, H-3e), 2.60 (broad s, 1H), 2.22 (t, J=12.7 Hz), 2.14, 2.12, 2.05, 2.04 and 1.91 (5s, 15H, O- and N-Ac methyl groups).

Sodium (2-chloro-5-(methoxy-5-chlorotricyclo [3.3.1.1$^{3,7}$]dec-2-ylidenemethyl)phenyl 5-acetamido-3,5-dideoxy-α-D-glycero-D-galacto-2-nonulopyranosid)onate (compound 5 in FIG. 2)

The impure pyranoside methyl (2-chloro-5-(methoxy-5-chlorotricyclo[3.3.1.1$^{3,7}$]dec-2-ylidenemethyl)phenyl 5-acetamido-4,7,8,9-tetra-O-acetyl-3,5-dideoxy-α-D-glycero-D-galacto-2-nonulopyranosid)onate (1.76 g, 2.1 mmole) was deprotected in a mixture of 6.5 ml of THF and 6.5 ml of MeOH with 12 ml of 1 N NaOH at 0° C. After sitting for 5 minutes at 0° C., the mixture was stirred at room temperature for one hour. Next, the pH was lowered by the addition of 1.05 g of solid sodium bicarbonate. Although most of the bicarbonate did not go into solution, a clear solution was ultimately obtained by dilution with water, which yielded a total volume of 100 ml.

Next, the solution was filtered through a Buchner funnel, rinsed with a small volume of water, and purified by reverse phase prep HPLC with a one-inch column packed with polystyrene. The column was eluted with an acetonitrile-water gradient. The fractions containing the product were then pooled and lyophilized to yield 658.9 mg (46.6%) of sodium (2-chloro-5-(methoxy-5-chlorotricyclo[3.3.1.1$^{3,7}$]dec-2-ylidenemethyl)phenyl 5-acetamido-3,5-dideoxy-α-D-glycero-D-galacto-2-nonulopyranosid)onate as a white fluffy powder.

$^1$H NMR (D$_2$O): δ 7.42 (d, J=8.1 Hz, 1H), 7.32 (broad s, 1H), 7.02 (d, J=8.1 Hz, 1H), 3.72–3.93 (m, 5H), 3.59–3.68 (m, 2H), 3.31 (s, 1H), 3.31 (s, 3H, OCH$_3$), 2.90–2.99 (m, 1H, H-3e), 2.67 (broad s, 1H), 2.08–2.30 (m, 6H, adamantyl), 2.02 (s, 3H, N-Ac), 1.66–2.0 (m, 5 adamantyl H and 1-H-3a).

Sodium (2-chloro-5-(4-methoxyspiro{1,2-dioxetane-3,2'-(5-chloro)tricyclor[3.3.1.1$^{3,7}$]decan}-4-yl-phenyl 5-acetamido-3,5-dideoxy-α-D-glycero-D-galacto-2-nonulopyranosid)onate (compound 6 in FIG. 2)

Photooxygenation of a solution of sodium (2-chloro-5-(methoxy-5-chlorotricyclo[3.3.1.1$^{3,7}$]dec-2-ylidenemethyl) phenyl 5-acetamido-3,5-dideoxy-α-D-glycero-D-galacto-2-nonulopyranosid)onate (414.5 mg, 0.635 mmole) in 20 ml of 15% MeOH in CH$_2$Cl$_2$ in the presence of 20 drops of TPP stock solution (2 mg/ml CHCl$_3$) was carried out by irradiation with a 400 w sodium vapor lamp for 25 minutes at a temperature of from 3–5° C while continuously bubbling oxygen through the solution. The reaction was monitored using the UV spectrum, i.e., the maximum absorptions of the product shifted from 260.5 nm to 277.5 nm as the reaction proceeded. Next, the mixture was concentrated on a rotovap at a low temperature and pumped in vacuo until a purple glassy foam was obtained. The crude product obtained was soluble in 30 ml of H$_2$O containing 2 ml of a saturated NaHCO$_3$ solution. The product was then filtered through a Buchner funnel and rinsed with water which yielded a final volume of 50 ml. The solution was then injected in 5 separate 10 mL portions on the reverse phase HPLC column described above. The column was eluted with an acetonitrile-water gradient. HPLC revealed that a broad peak eluted just before the sharp major peak. These fractions were pooled and lyophilized separately to yield 68.4 mg and 350 mg respectively, as white powders. Both product fractions exhibited chemiluminescence upon treatment with neuraminidase enzyme (recombinant from E. Coli) obtained from Oxford Glycosciences.

Sodium (5-(4-methoxyspiro{1,2-dioxetane-3,2'tricyclo[3.3.1.1$^{3,7}$]decan}-4-yl-phenyl 5-acetamido-3,5-dideoxy-α-D-glycero-D-galacto-2-nonulopyranosid)onate was prepared from the corresponding acetate-protected, phase-transfer coupled enol ether in the same manner as described above and then de-protected and photooxygenated. Spotting the product on a TLC plate from an aqueous solution exhibited blue chemiluminescence when the plate was heated in the dark. This phenomenon indicated the presence of a 1,2-dioxetane product.

The synthesis set forth above is a representative example of the formation of a 1,2-dioxetane substrate according to the present invention which is capable of detecting the presence of neuraminidase in a sample and should not be construed as limiting the scope of the present invention. Other 1,2-dioxetanes, such as longer wave length emitting dioxetanes with naphthalene or heteroaryl emitters are considered within the scope of the invention. Additionally, the presence of stabilizing groups such as dialkyl dioxetanes and adamantyl or substituted adamantyl groups are also contemplated within the scope of the present invention.

The 1,2-dioxetanes of the present invention are engineered to detect the presence of neuraminidase in a two-step assay as is set forth in FIG. 3. In the two-step assay, the neuraminidase acts in step 1. In step 2, the liberated dioxetane is triggered with a base alone or with a base and a monometric or oligomeric enhancer moiety which may additionally contain an energy acceptor device for additional amplification of light emission, or the shifting of its wave length. Suitable bases include metal hydroxides, carbonates and the like, to as well as ammonia and amine bases. The two step assay for the detection of neuraminidase is derived from the basic protocol disclosed by M. Potier, et al., Anal. Biochem., 94, 287–296, 1979, which indicates a first step at a pH below 7 followed by the application of an upward pH shift to about pH 10 (or higher) will produce a fluorescent signal from the enzyme product.

EXPERIMENT 1

Figure 5:
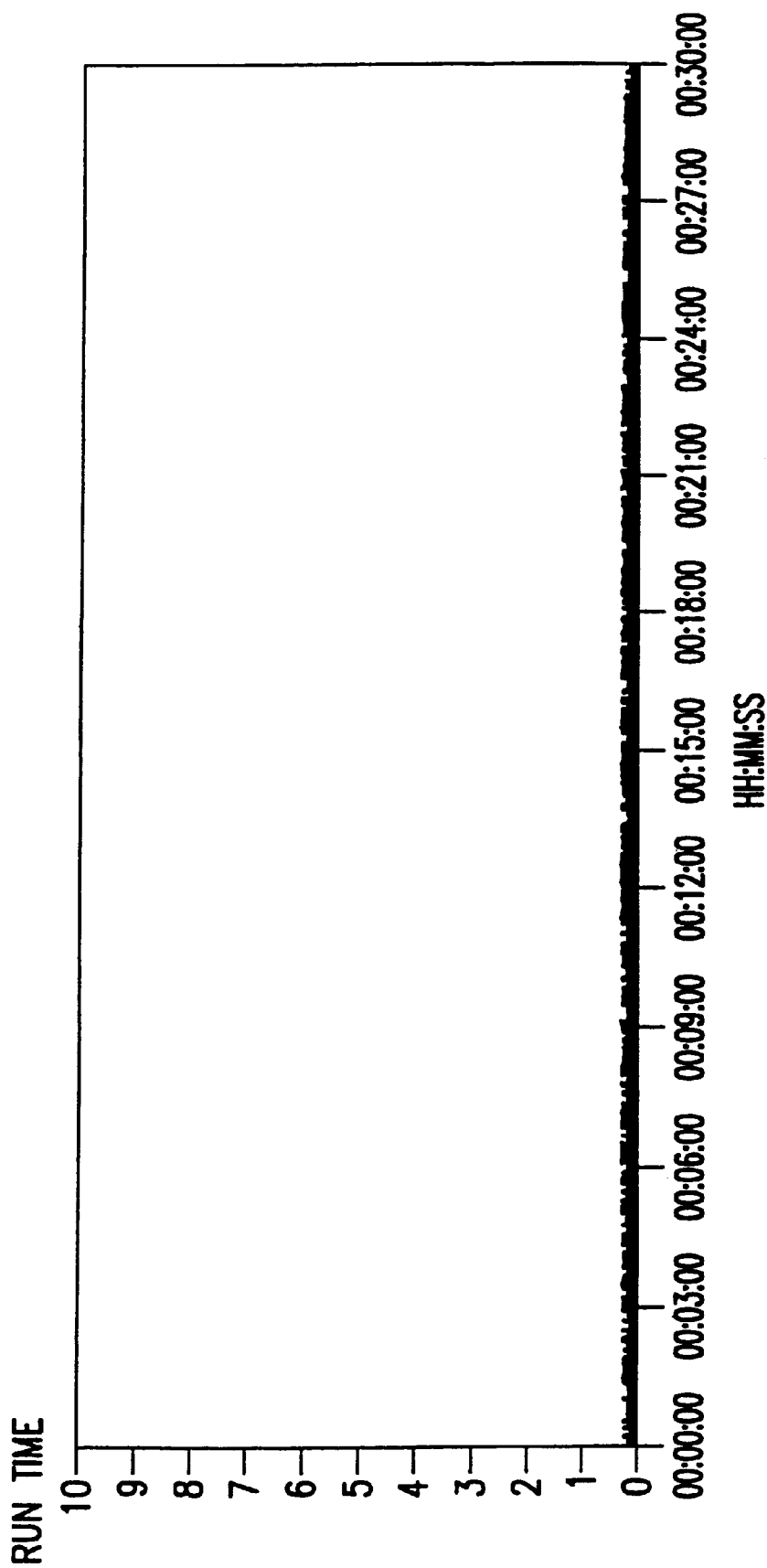
FIG. 5 provides graphic illustration of the background noise obtained from 5 µl of dioxetane stock diluted with 250 µl of glaxo buffer with no enzyme.

1.5 mg of dioxetane 489-102 (the compound of FIG. 1) (molecular weight of 684.5) was dissolved in 0.5 ml of 0.51 M sodium acetate buffer at a pH of about 8.3 to form a dioxetane stock solution. FIG. 5 is a plot indicating the noise obtained from 5 microliters of the dioxetane stock diluted with 250 microliters of a glaxo pH 5.5 buffer (no enzyme). As shown, there was essentially constant noise at approximately 0.2 RLU.

Figure 4:
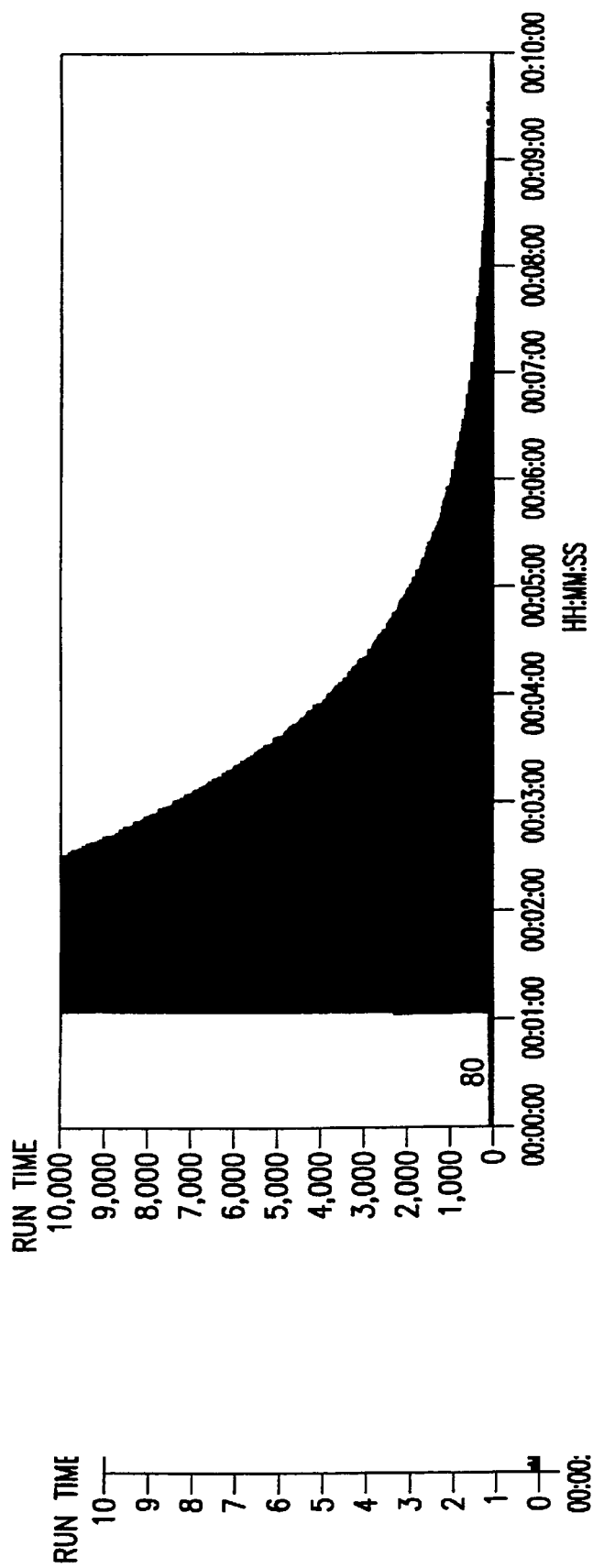
FIG. 4 provides graphic illustration of the chemiluminescent signal obtained by neuraminidase triggering of a 1,2-dioxetane neuraminidase substrate from Experiment 1.

Next, 0.2 units of Oxford Enzyme were diluted with 400 microliters of Oxford Enzyme. 200 microliters of the enzyme (0.1 units) were then treated with 10 microliters of the dioxetane stock and incubated at 37° C. for 15 minutes. The solution was then placed in a Turner luminometer. Light was detected at a constant 80 RLU at a pH of 5.5. All Turner readings were calibrated to 31.5° C. 400 microliters of 0.1 AMP with a pH of 10 was then injected into the tube to produce a peak light emission of greater than 10,000, decaying with a half life of about 1.25 minutes. The form of the curve in FIG. 4 indicates a near complete substrate consumption during the incubation time.

EXPERIMENT 2

Figure 6:
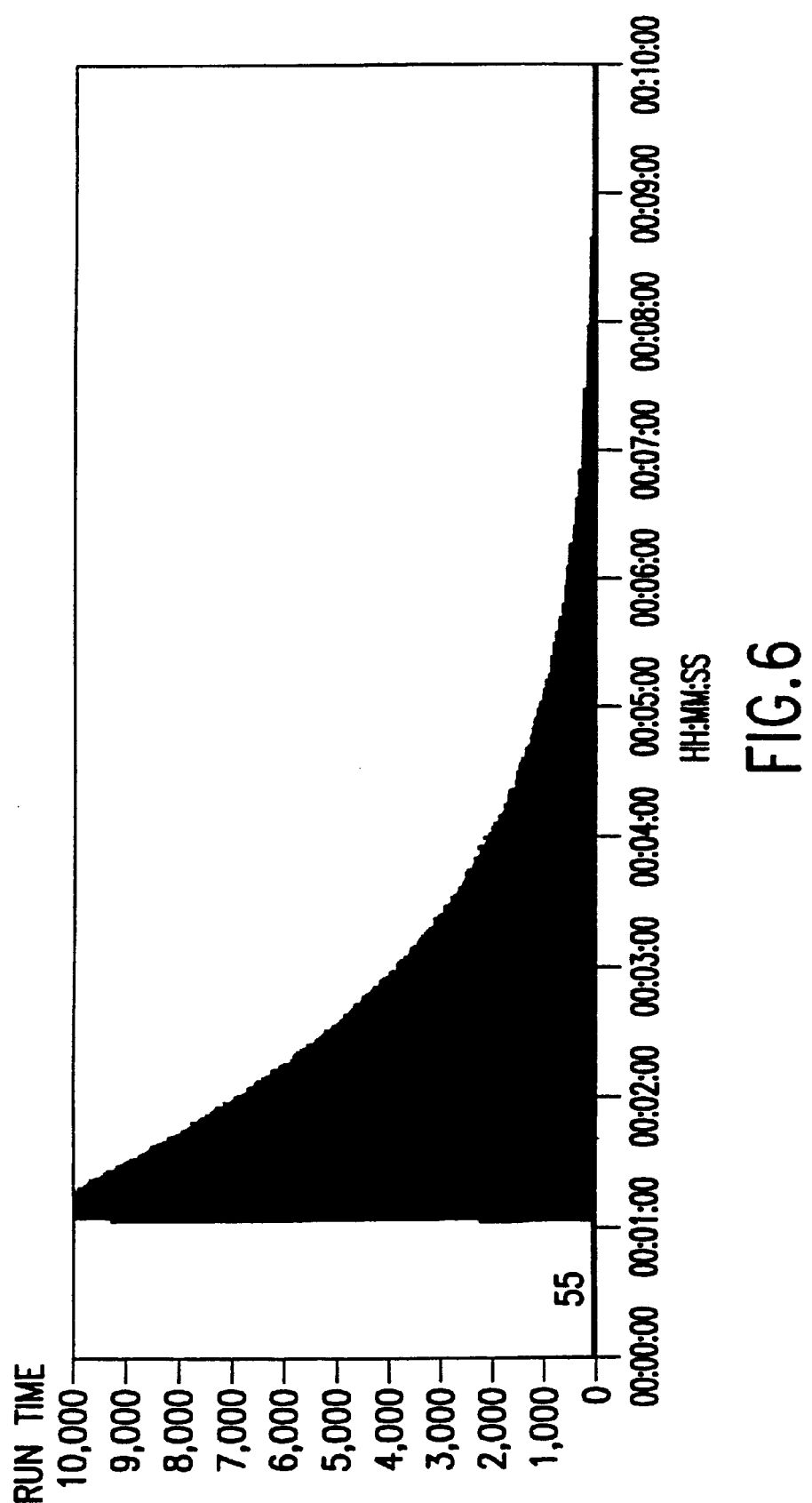
FIG. 6 provides graphic illustration of the chemiluminescent signal obtained from Experiment 2.

5 microliters of the dioxetane stock prepared in Experiment 1 was added to 0.05 units of Oxford sialidase in 200 microliters of the pH 5.5 buffer. The solution (approximately a 110 micromolar substrate) was incubated at 37° C. for 15 minutes. The solution was then placed in a Turner luminometer, and steady light emission at about 55 RLU was noted (see FIG. 6). This light emission is about 275 times greater than the "no enzyme" noise at pH 5.5 as shown in FIG. 5. Next, 400 microliters of AMP pH 10 buffer was injected to produce an off-scale light spike (i.e., greater than 10,000 RLU).

EXPERIMENT 3

Figure 7:
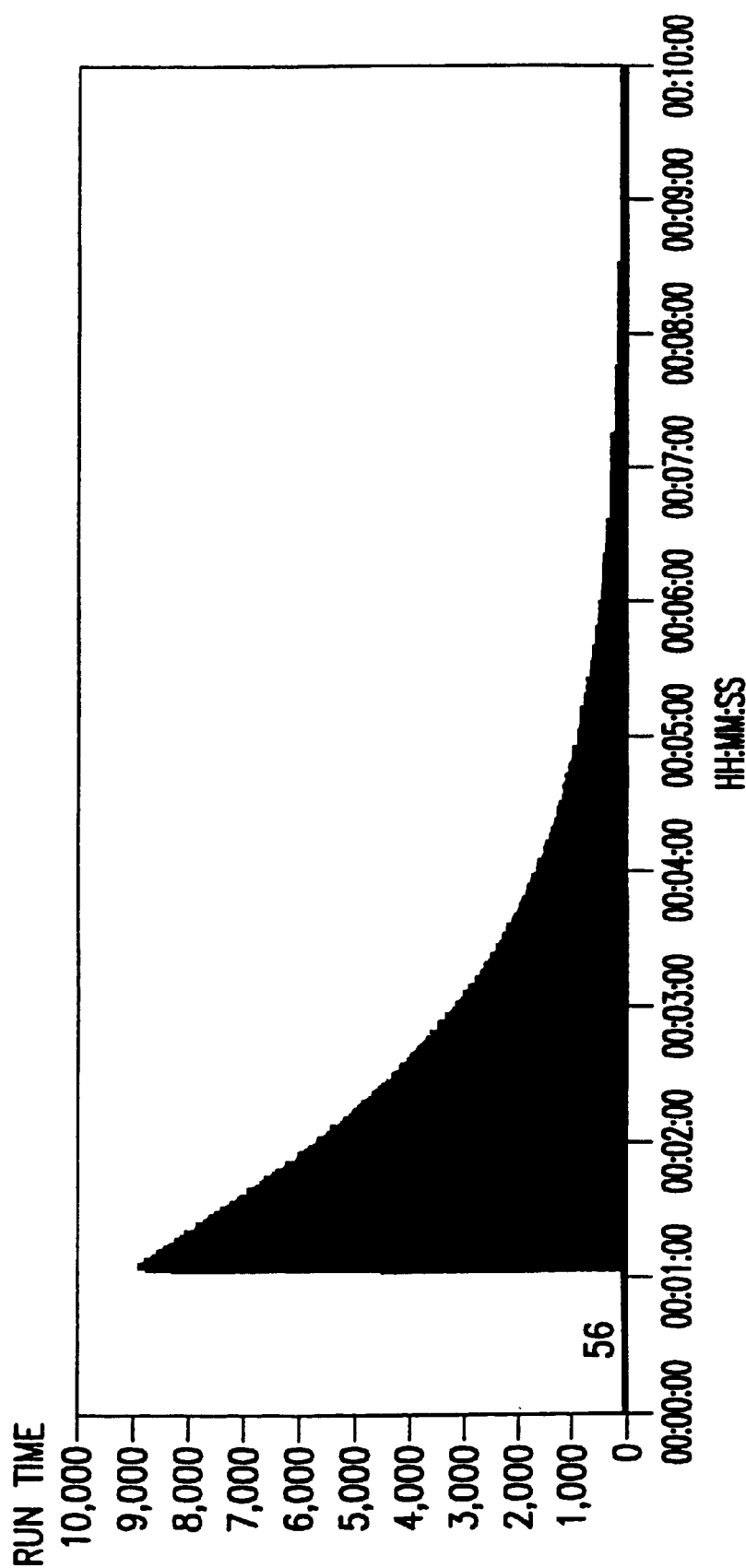
FIG. 7 provides graphic illustration of the chemiluminescent signal obtained from Experiment 3.

Experiment 2 was repeated with a 110 micromolar substrate in the presence of 0.025 units of the enzyme. FIG. 7 illustrates that at a pH of 5.5, the light level obtained (56 RLU) was similar to that obtained in Experiment 2. From these results it was determined that the light emission at pH 5.5 did not correlate with enzyme concentration. Next, an additional 400 microliters of the AMP pH 10 buffer was added, which produced a light peak at 8860 RLU and similar decay kinetics as in Experiment 2.

EXPERIMENT 4

Figure 8:
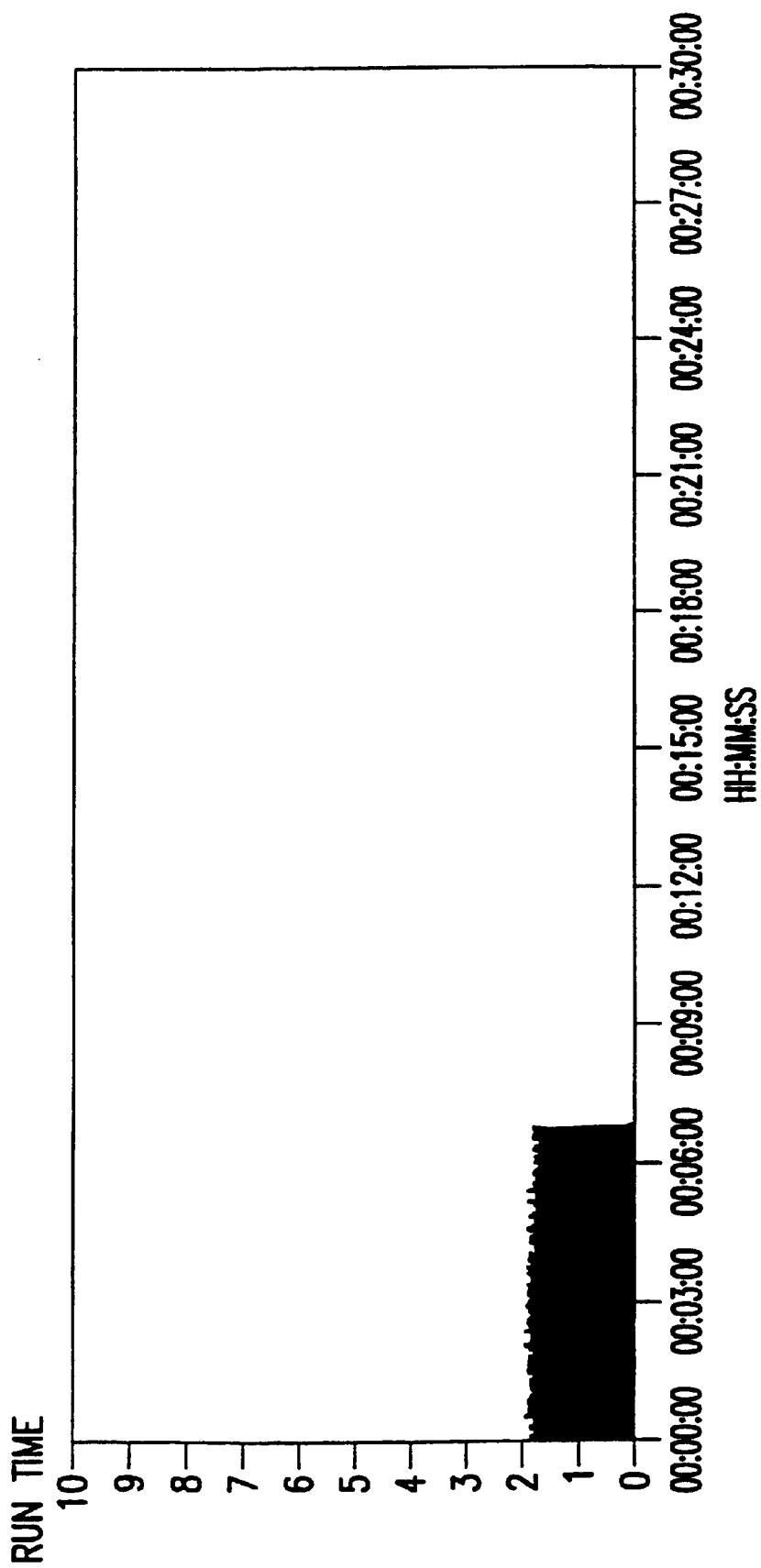
FIG. 8 provides graphic illustration of the background noise from 5 ml of dioxetane stock diluted with 250 ml of sodium phosphate buffer with no enzyme.

A 120 micromolar sodium phosphate buffer with a pH of 7.7 was prepared from stock solutions of monobasic and dibasic salts. 250 microliters of this buffer and 5 microliters of the dioxetane stock solution prepared in Experiment 1 were incubated in a Turner luminometer at 31.5° C. FIG. 8 demonstrates a steady noise level at about 2 RLU at a pH of 7.7. This is 10 times the noise level at pH 5.5 (no enzyme) as shown in Experiment 1.

EXPERIMENT 5

Figure 9:
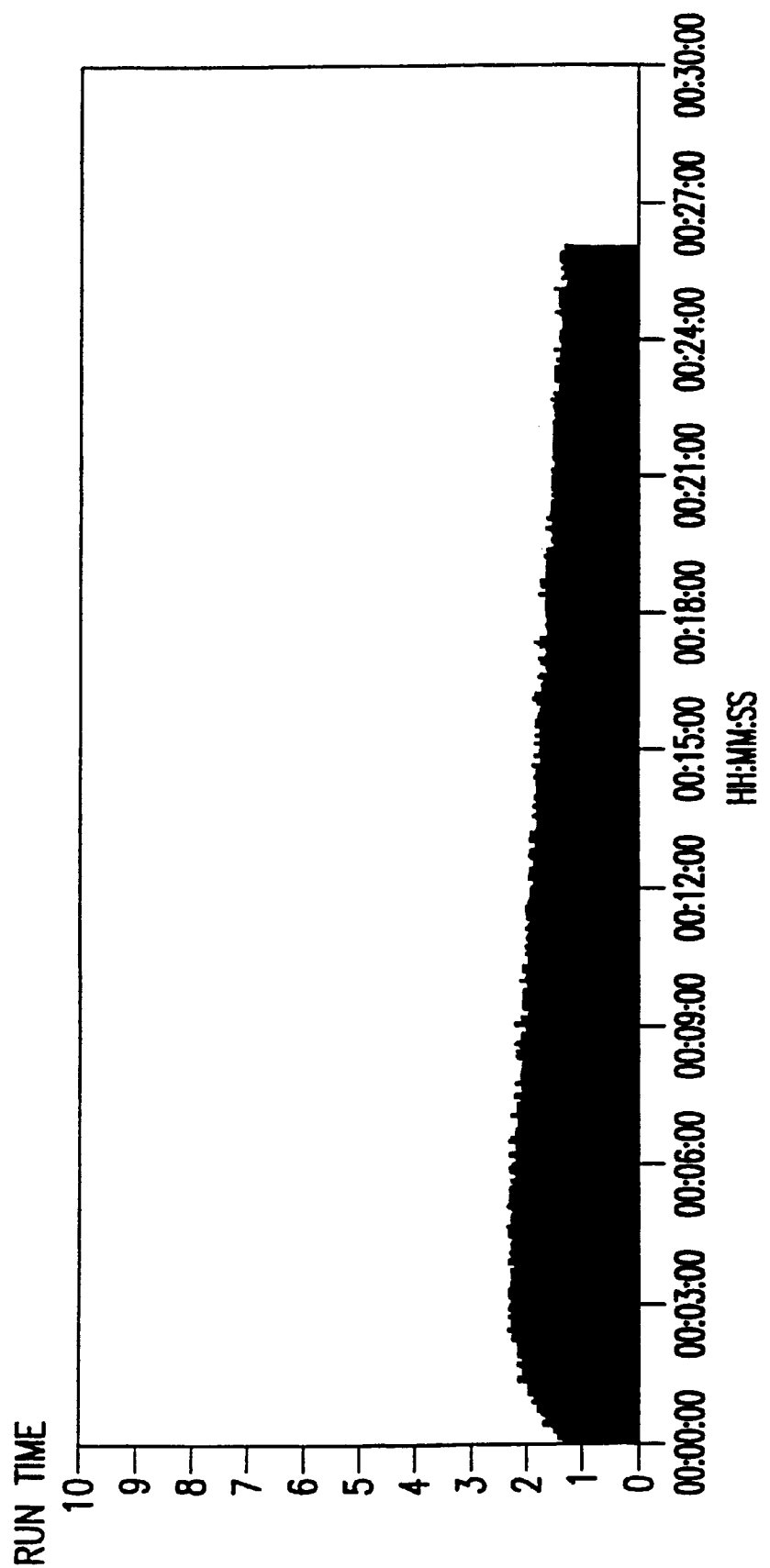
FIG. 9 provides graphic illustration of the chemiluminescent signal obtained from Experiment 5.

The experimental conditions are the same as those set forth in Experiment 4, except that a pH 10 AMP buffer was used in place of the sodium phosphate buffer. This experiment showed noise at 31.5° C., with a maximum value of about 2.3 RLU. As can be seen in FIG. 9, the noise slowly decreased over a time period of 20 minutes to approximately 1.3 RLU. The substrate used in this Experiment did not receive up-front incubation other than cold storage in the acetate buffer.

EXPERIMENT 6

Figure 10:
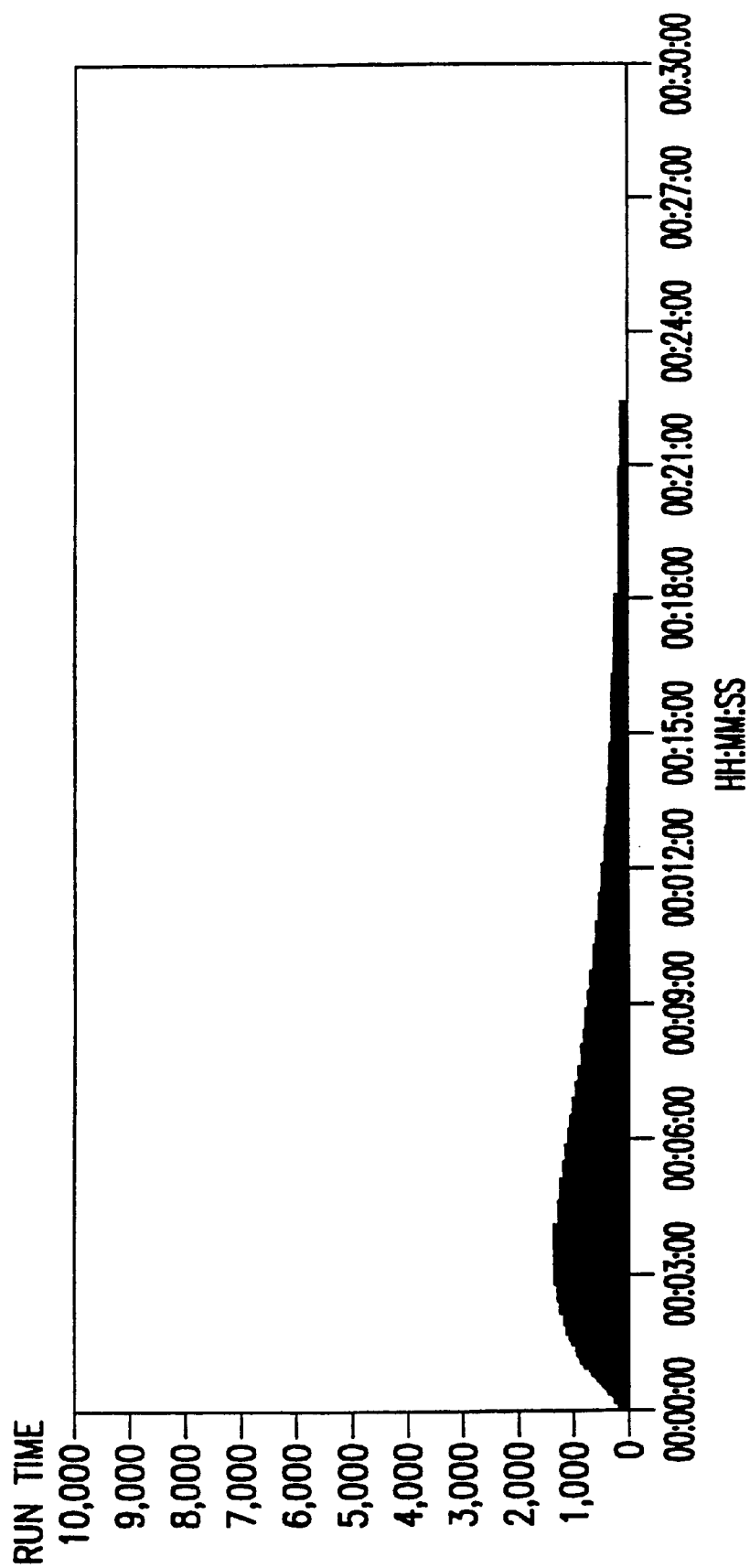
FIG. 10 provides graphic illustration of the chemiluminescent signal obtained from Experiment 6.

A pH 7.7 solution of 5 microliters of dioxetane stock and 200 microliters of the phosphate buffer was made and incubated for several minutes at 31.5° C. After incubation, 0.25 units of Oxford sialidase in 50 microliters of 50 micromolar acetate buffer was added. Chemiluminescence was spontaneously produced, rising to a maximum of 1380 RLU at 3.25 minutes (see FIG. 10). The approximate half life in the decay portion of the curve was about 5.5 minutes.

EXPERIMENT 7

Figure 11B:
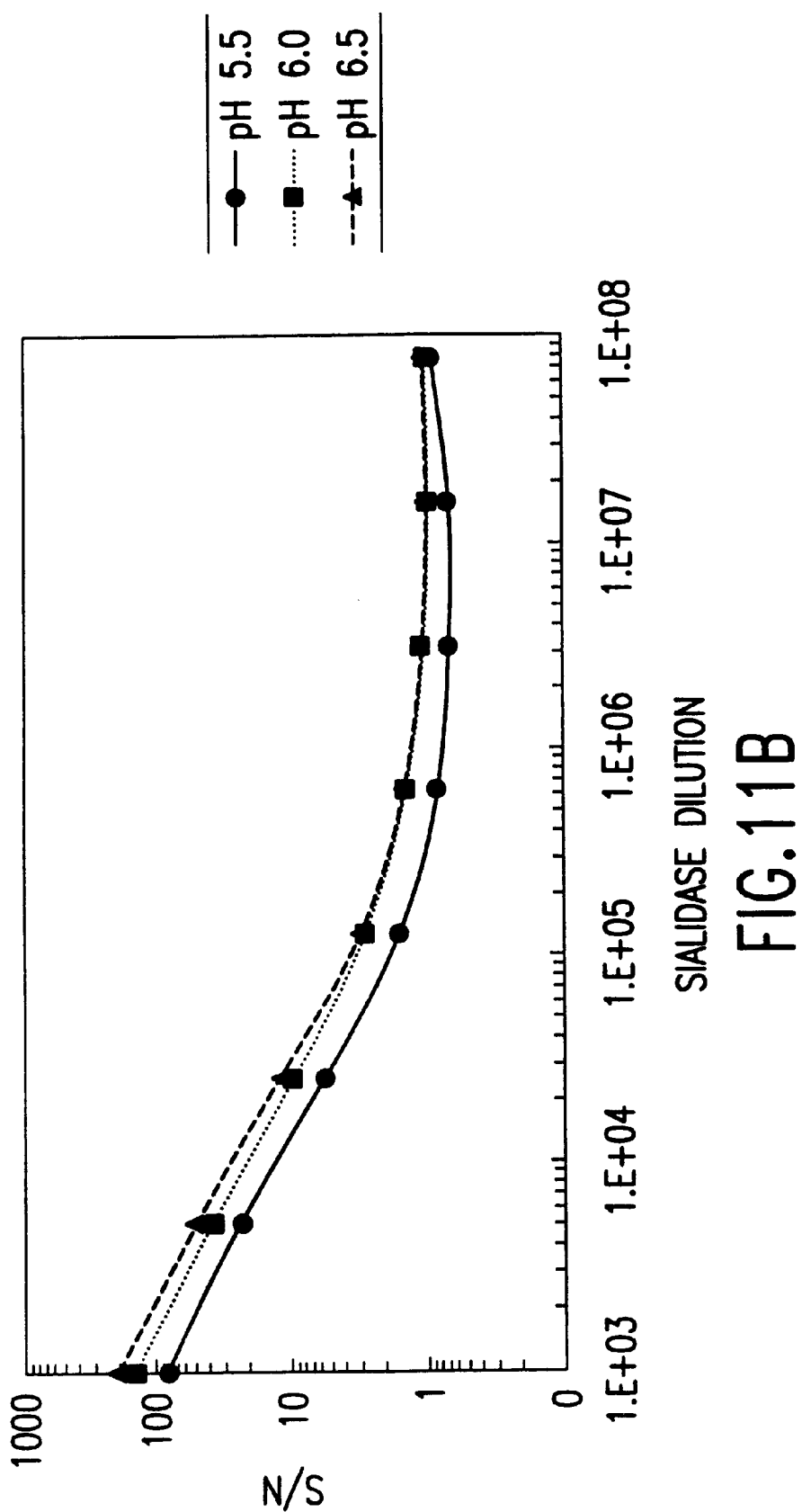
FIG. 11B is a graph showing signal to noise ratio (S/N) as a function of sialidase dilution for a substrate according to the invention in a 0.05 M sodium acetate/0.1M NaCl buffer.

A two step assay was conducted with the Oxford X-501 neuraminidase enzyme utilizing a quaternary onium polymeric enhancer and a base in step two. These conditions permitted the detection of $2.7 \times 10^{-7}$ units of enzyme and a signal-to-noise ratio of approximately 2.0. The enzyme exhibited 300 units of activity per mg and had a molecular weight of 41,000. The unoptimized, lower detection limit was $2.19 \times 10^{-15}$ moles of enzyme. This corresponds to a 1:125,000 dilution of the Oxford enzyme solution. The assay was carried out in 0.05 M sodium acetate/0.1 M NaCl buffer solution at a pH of 5.5, 6.0, and 6.5. The results and conditions are summarized in Table A and depicted graphically in FIGS. 11A and 11B.

TABLE A

| Units sialidase per well | Dilution | pH 5.5 RLU | S/N | pH 6.0 RLU | S/N | pH 6.5 RLU | S/N |
|---|---|---|---|---|---|---|---|
| | Blank | 5791.00 | 5507.00 | 4244.00 | 4708.00 | 2047.00 | 2085.50 |
| | Blank | 5223.00 | | 5172.00 | | 2124.00 | |
| 1.70667E-11 | 1953125000 | 5515.50 | 1.00 | 4580.50 | 0.97 | 2110.50 | 1.01 |
| 8.53333E-11 | 390625000 | 6057.00 | 1.10 | 4809.50 | 1.02 | 2141.50 | 1.03 |
| 4.26667E-10 | 78125000 | 5226.50 | 0.95 | 4830.00 | 1.03 | 2316.00 | 1.11 |
| 2.13333E-09 | 15825000 | 4024.50 | 0.73 | 4801.00 | 1.02 | 2301.00 | 1.10 |
| 1.06667E-08 | 3125000 | 3926.50 | 0.71 | 5341.00 | 1.13 | 2374.00 | 1.14 |
| 5.33333E.08 | 625000 | 4875.50 | 0.89 | 7005.50 | 1.49 | 3277.00 | 1.57 |
| 2.66667E-07 | 125000 | 9278.50 | 1.68 | 14161.00 | 3.01 | 7106.00 | 3.41 |
| 1.33333E-06 | 25000 | 32671.00 | 5.93 | 48058.00 | 10.21 | 26764.50 | 12.83 |
| 6.66667E.06 | 5000 | 133228.00 | 24.19 | 180955.50 | 38.44 | 106454.00 | 51.04 |
| 3.33333E-05 | 1000 | 463115.00 | 84.10 | 656939.00 | 139.54 | 412963.50 | 198.03 |

Figure 12B:
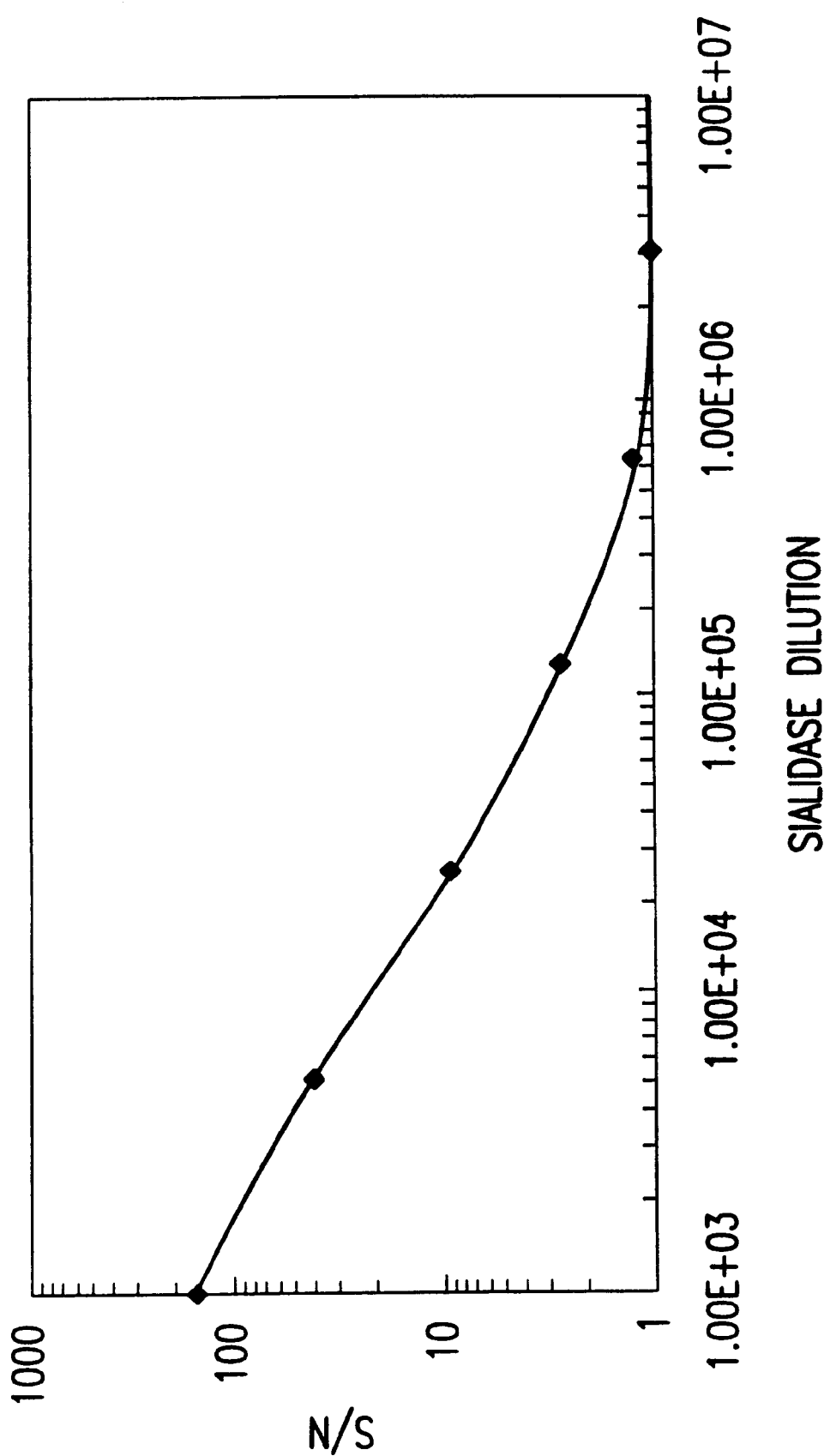
FIG. 12B is a graph showing signal to noise ratio (S/N) as a function of sialidase dilution for a methylumbelliferyl-N-acetylneuraminic acid salt fluorescent substrate in a 0.05 M sodium acetate/0.1M NaCl buffer.

Experiments with Sigma's Methylumbelliferyl-N-acetylneuraminic acid salt as a fluorescent substrate gave a signal-to-noise ratio of 1.79 at a dilution of 1:40,000, indicating inferior sensitivity compared to that obtained with the chemiluminescent neuraminidase-Star substrate. The results and conditions are summarized in Table B and depicted graphically in FIGS. 12A and 12B.

TABLE B

| Dilution | RLU | S/N |
|---|---|---|
| 1000 | 4209078 | 153.62 |
| 5000 | 1171002 | 42.74 |
| 25000 | 263218 | 9.61 |
| 125000 | 75078 | 2.74 |
| 625000 | 32200 | 1.18 |
| 3125000 | 27538 | 1.01 |
| 15625000 | 28231 | 0.96 |

EXPERIMENT 8

Figure 13A:
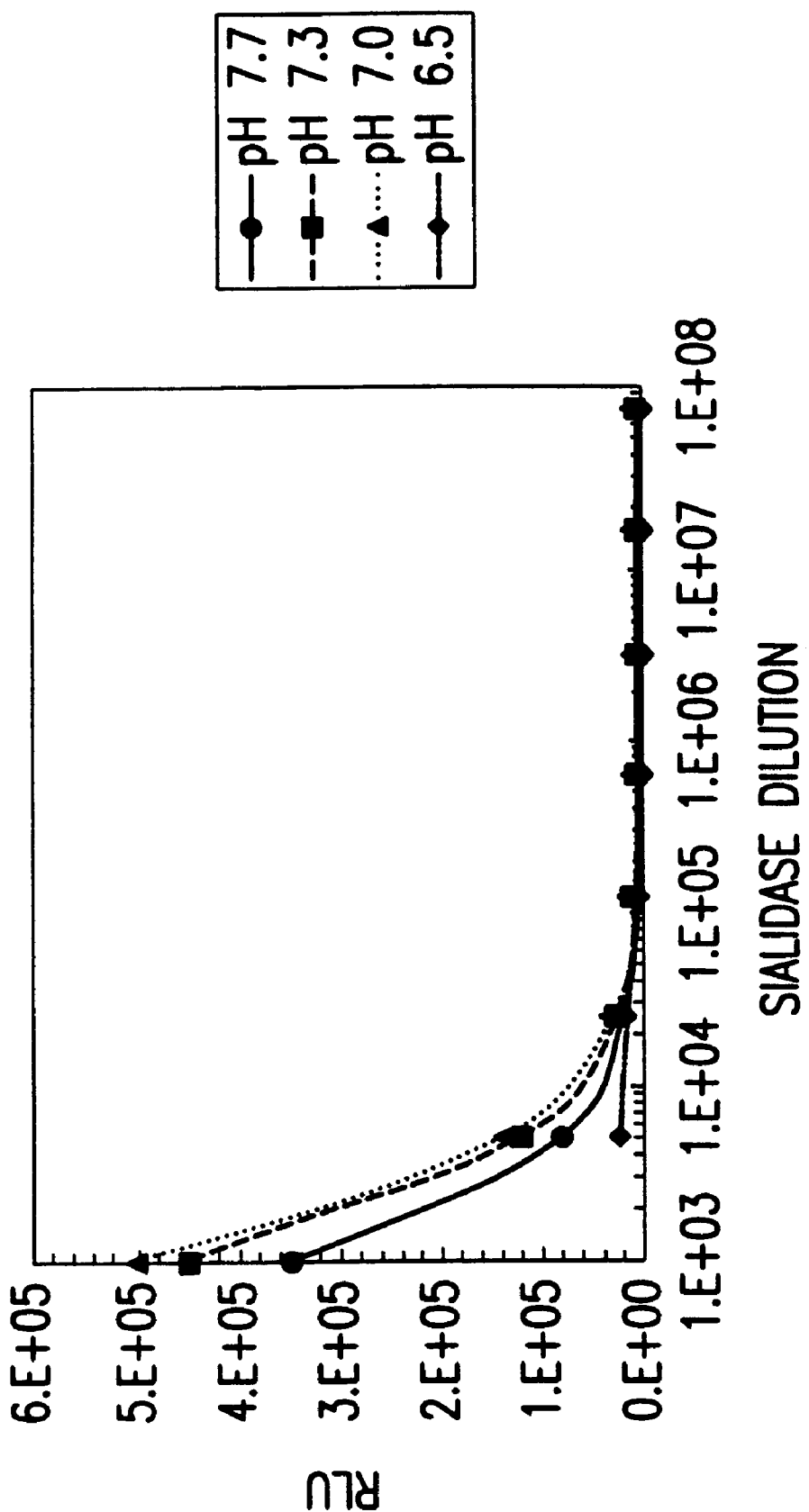
FIG. 13A is a graph showing chemiluminescence (RLU) as a function of sialidase dilution for a substrate according to the invention in a 0.05 M phosphate/0.1M NaCl buffer.
Figure 13B:
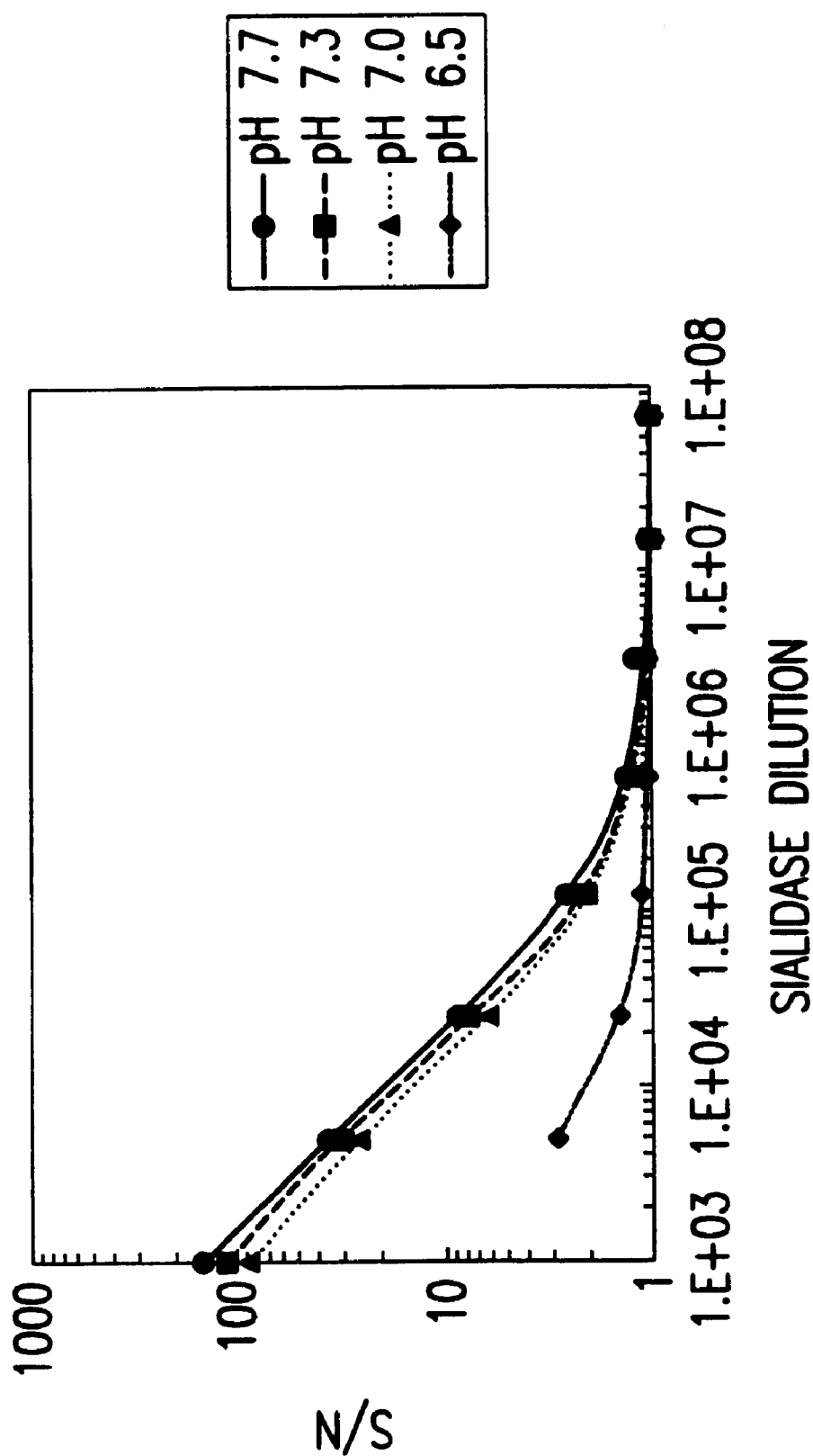
FIG. 13B is a graph showing signal to noise ratio (S/N) as a function of sialidase dilution for a substrate according to the invention in a 0.05 M phosphate/0.1M NaCl buffer.

The two step assay of Experiment 7 was carried out using a 0.05 M phosphate/0.1 M NaCl buffer in place of the 0.05 M sodium acetate buffer. The assays were carried out at a pH of 7.7, 7.3, 7.0, and 6.5. The results and conditions are summarized in Table C and depicted graphically in FIGS. 13A and 13B.

TABLE C

| Sialidase, units/well | Sialidase dilution | pH 7.7 | S/N | pH 7.3 | S/N | pH 7.0 | S/N | pH 6.5 | S/N |
|---|---|---|---|---|---|---|---|---|---|
| 3.33333-05 | 1000 | 348406.00 | 152.41 | 448301.00 | 115.07 | 502029.00 | 94.68 | | |
| 6.66667E-06 | 5000 | 81881.00 | 35.82 | 121922.00 | 31.29 | 140195.00 | 26.44 | 21972.00 | 2.85 |
| 1.33333E-06 | 25000 | 20034.50 | 8.76 | 27813.00 | 7.14 | 33429.50 | 6.30 | 10740.00 | 1.40 |
| 2.66667E-07 | 125000 | 5923.50 | 2.59 | 8416.50 | 2.16 | 10673.00 | 2.01 | 8240.00 | 1.07 |
| 5.33333E-08 | 625000 | 2920.50 | 1.28 | 4816.50 | 1.24 | 6462.50 | 1.22 | 7744.50 | 1.01 |
| 1.06667E-08 | 3125000 | 2593.00 | 1.13 | 4113.50 | 1.06 | 5743.50 | 1.08 | 7626.50 | 0.99 |
| 2.13333E-09 | 15625000 | 2327.50 | 1.02 | 3910.50 | 1.00 | 5536.50 | 1.04 | 7440.50 | 0.97 |
| 4.26667E-10 | 78125000 | 2332.50 | 1.02 | 3748.00 | 0.96 | 5468.50 | 1.03 | 7763.00 | 1.01 |
| 8.53333E-11 | 390625000 | 2339.50 | 1.02 | 3719.50 | 0.95 | 5274.00 | 0.99 | 7908.00 | 1.03 |
| 1.70667E-11 | 1953125000 | 2353.50 | 1.03 | 3731.50 | 0.96 | 5162.00 | 0.97 | 8090.00 | 1.05 |
| | | 2341.50 | | 3820.50 | | 5341.50 | | 7683.00 | |
| | | 2354.50 | | 3971.50 | | 5265.00 | | 7709.00 | |

EXPERIMENT 9

Figure 14A:
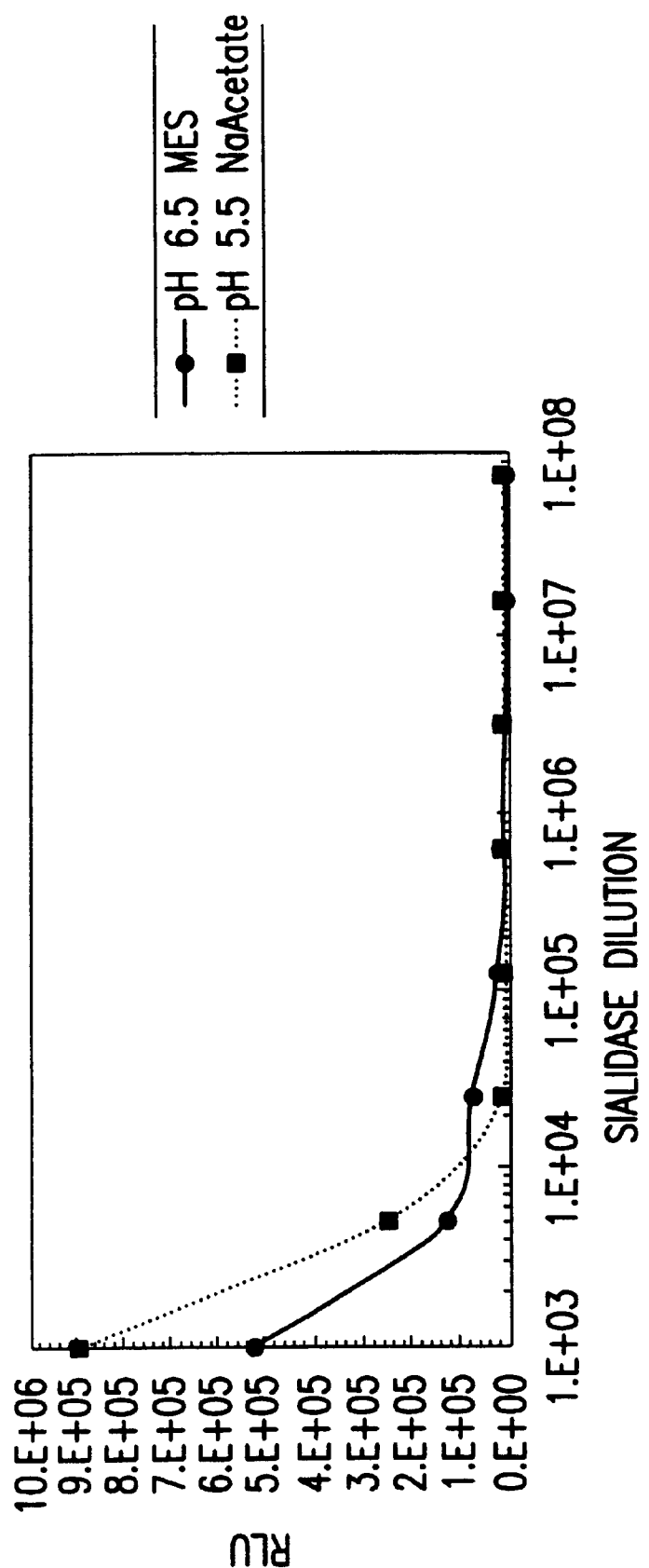
FIG. 14A is a graph showing chemiluminescence (RLU) as a function of sialidase dilution for a substrate according to the invention using two different buffer systems.
Figure 14B:
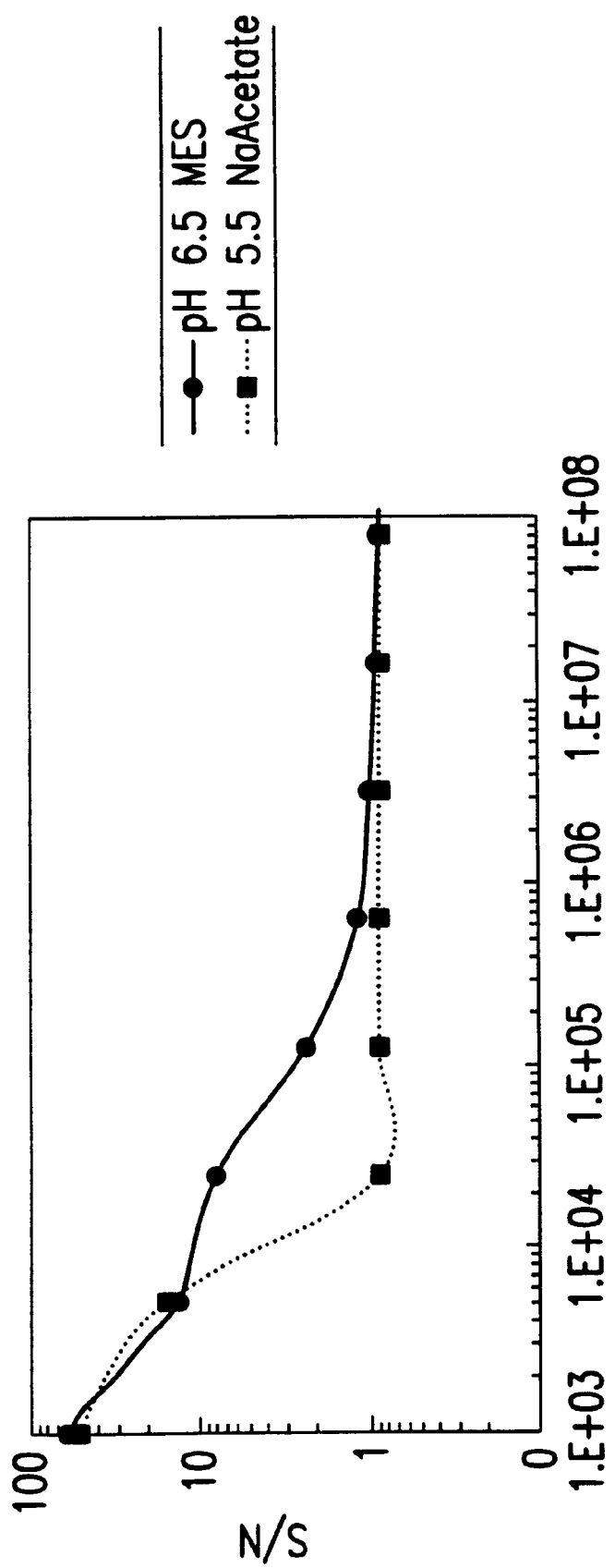
FIG. 14B is a graph showing signal to noise ratio (S/N) as a function of sialidase dilution for a substrate according to the invention using two different buffer systems.

A two step assay was conducted with the Oxford X-501 neuraminidase enzyme utilizing a quaternary onium polymeric enhancer and a base in step 2. The conditions were the same as in Experiment 7, except that two different buffer systems were used as a means of comparison: MES at a pH of 6.5 and sodium acetate at a pH of 5.5. The results and conditions are summarized in Table D and depicted graphically in FIGS. 14A and 14B.

EXPERIMENT 10

Figure 15A:
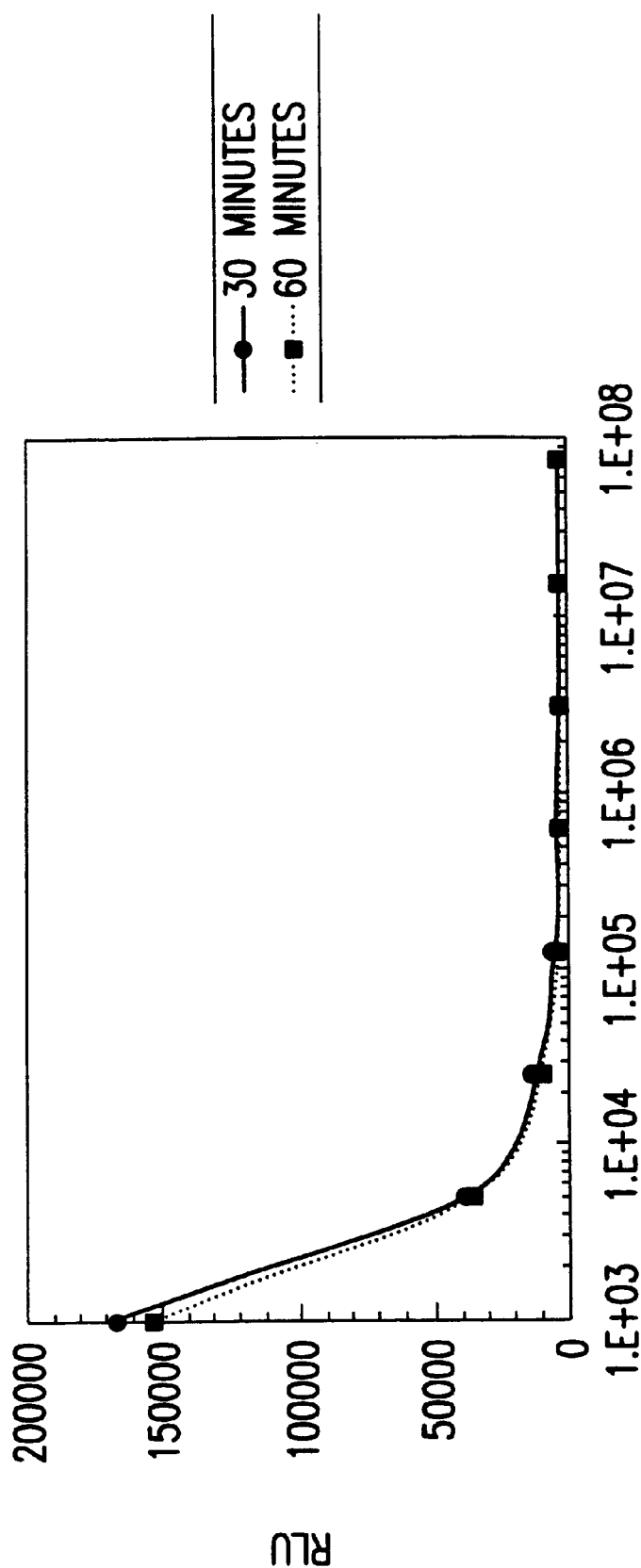
FIG. 15A is a graph showing chemiluminescence (RLU) as a function of sialidase dilution for a substrate according to the invention in a 0.05 M phosphate/0.1M NaCl buffer at a pH of 7.7.
Figure 15B:
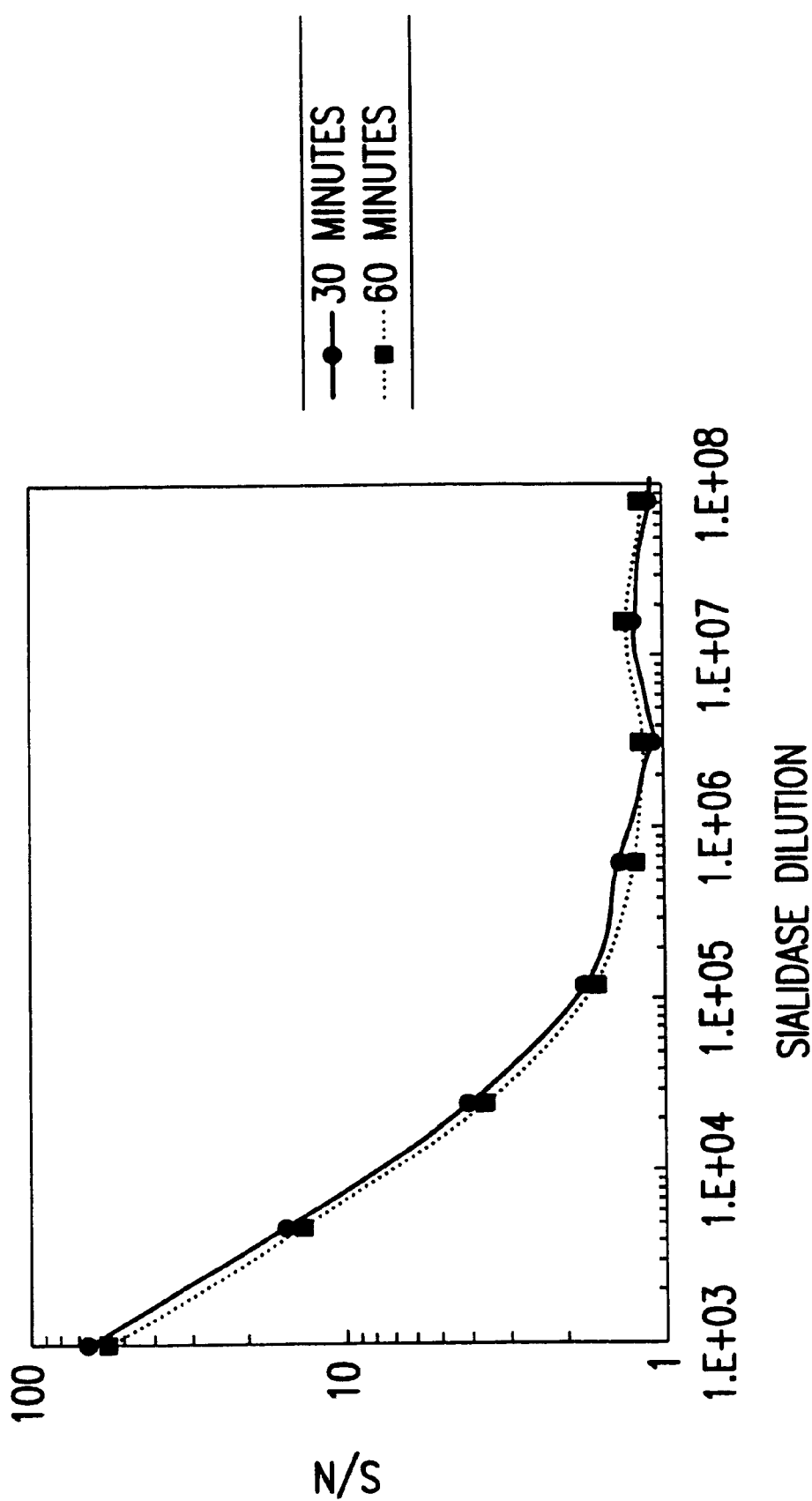
FIG. 15B is a graph showing signal to noise ratio (S/N) as a function of sialidase dilution for a substrate according to the invention in a 0.05 M phosphate/0.1M NaCl buffer at a pH of 7.7.

A two step assay was conducted with the Oxford X-501 neuraminidase enzyme utilizing a quaternary onium polymeric enhancer and a base in step 2. The neuraminidase substrate was incubated at 37° C. in a 0.05 M phosphate/0.1 M NaCl, pH 7.7 buffer solution for 30 and 60 minutes. The results and conditions are summarized in Table E and depicted graphically in FIGS. 15A and 15B.

TABLE D

| Sialidase, units/well | Sialidase dilution | RLU, pH 6.5 | | S/N pH 6.5 | RLU, pH 5.5 | | S/N, pH 5.5 |
|---|---|---|---|---|---|---|---|
| 3.33E-05 | 1000 | 523391.00 | | 58.08 | 890934.00 | | 56.37 |
| 6.67E-06 | 5000 | 131643.33 | | 14.61 | 252815.67 | | 16.00 |
| 1.33E-06 | 25000 | 76867.67 | | 8.53 | 14715.33 | | 0.93 |
| 2.67E-07 | 125000 | 22911.67 | | 2.54 | 15090.33 | | 0.95 |
| 5.33E-08 | 625000 | 11516.00 | | 1.28 | 15294.67 | | 0.97 |
| 1.07E-08 | 3125000 | 10015.00 | | 1.11 | 15327.00 | | 0.97 |
| 2.13E-09 | 15625000 | 9234.67 | | 1.02 | 15527.67 | | 0.98 |
| 4.27E-10 | 78125000 | 8863.67 | | 0.98 | 15369.00 | | 0.97 |
| 8.53E-11 | 390625000 | 9128.00 | | 1.01 | 15455.67 | | 0.98 |
| 1.71E-11 | 1953125000 | 9096.00 | | 1.01 | 15361.33 | | 0.97 |
| | | 9027.00 | 9011.17 | | 15733.33 | 15804.00 | |
| | | 8995.33 | | | 15874.67 | | |

TABLE E

| Sialidase, units/well | Sialidase dilution | 30 minutes at 37 degrees | | 60 minutes at 37 degrees | |
|---|---|---|---|---|---|
| | | Ave RLU | S/N | Ave RLU | S/N |
| 3.33E-05 | 1000 | 167304.8 | 66.65183 | 153543.8 | 57.03176 |
| 6.67E-06 | 5000 | 38770.25 | 15.44551 | 36162.75 | 13.43217 |
| 1.33E-06 | 25000 | 10236.5 | 4.078076 | 9611.75 | 3.570155 |
| 2.67E-07 | 125000 | 4264.25 | 1.698816 | 4308.5 | 1.600334 |
| 5.33E-08 | 625000 | 3312 | 1.319454 | 3248.25 | 1.206519 |
| 1.07E-08 | 3125000 | 2646 | 1.054129 | 2985.75 | 1.109017 |
| 2.13E-09 | 15625000 | 2970.75 | 1.183504 | 3361.25 | 1.248491 |
| 4.27E-10 | 78125000 | 2667.75 | 1.062794 | 2964.75 | 1.101216 |
| 8.53E-11 | 390625000 | 2705.5 | 1.077833 | 3002.25 | 1.115145 |
| 1.71E-11 | 1953125000 | 2676 | 1.06608 | 2731.25 | 1.014486 |
| | | 2510.125 | | 2692.25 | |

EXPERIMENT 11

Figure 16A:
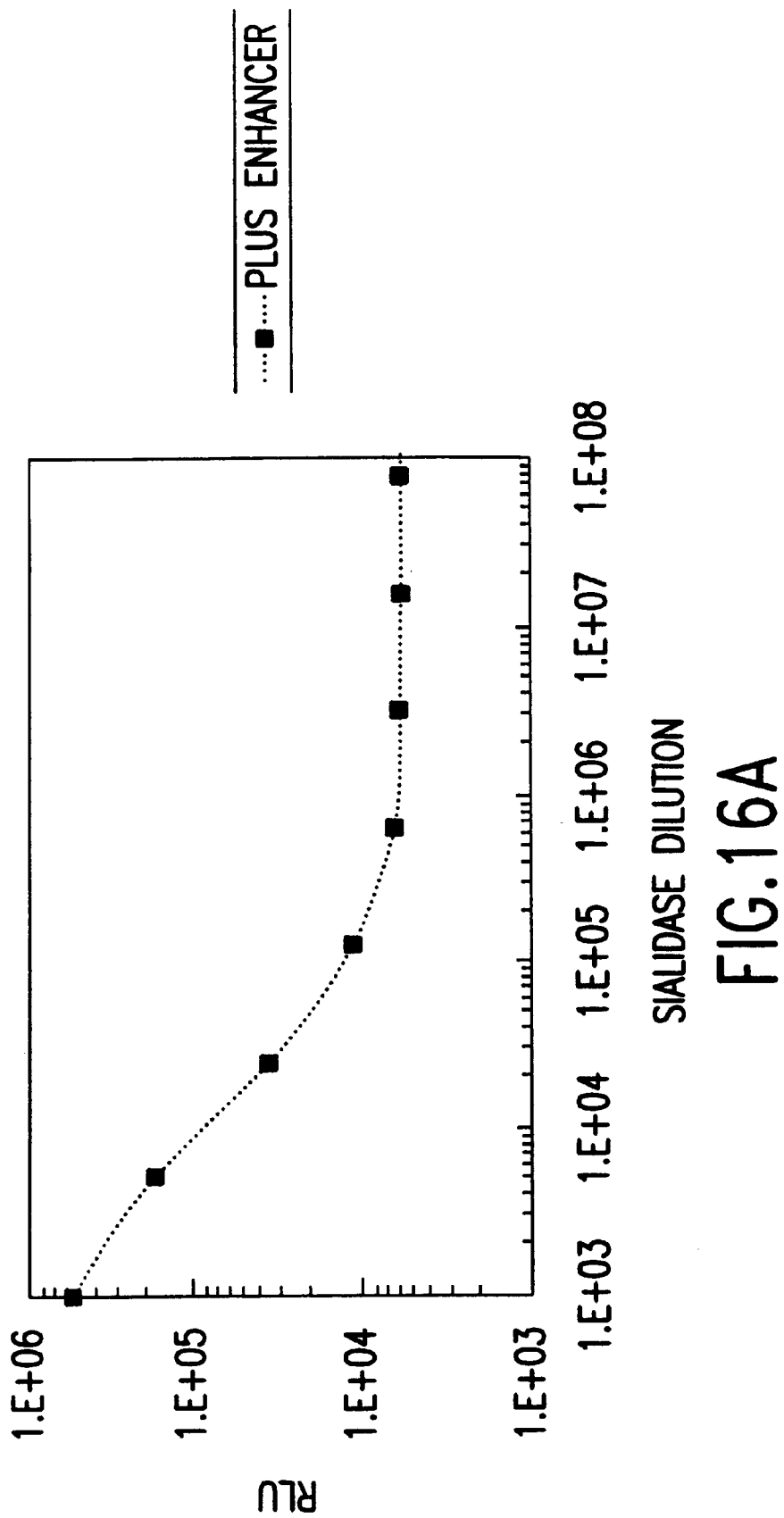
FIG. 16A is a graph showing chemiluminescence (RLU) as a function of sialidase dilution for a substrate according to the invention with a quaternary polymeric onium enhancer.
Figure 16B:
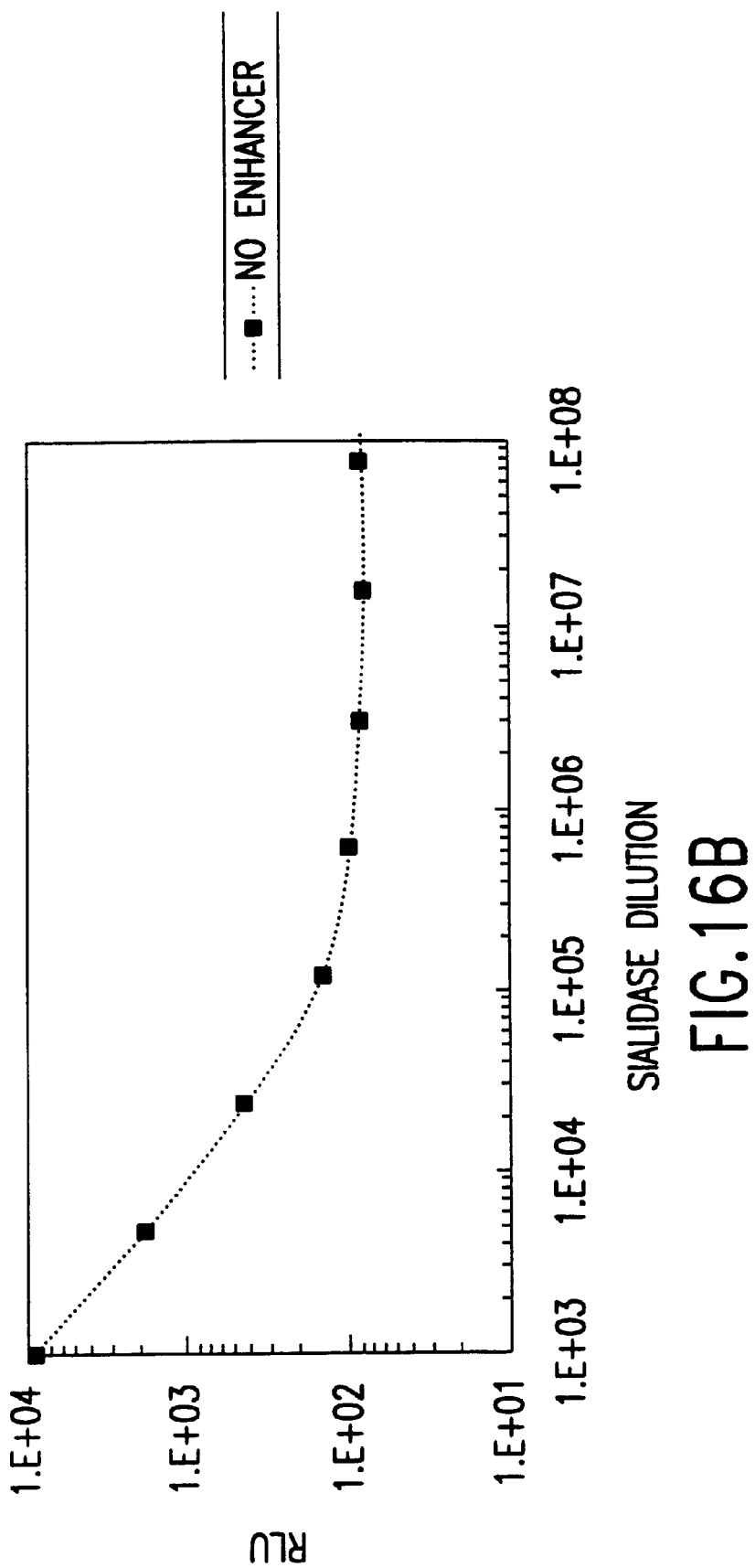
FIG. 16B is a graph showing chemiluminescence (RLU) as a function of sialidase dilution for a substrate according to the invention without a quaternary polymeric onium enhancer.
Figure 16C:
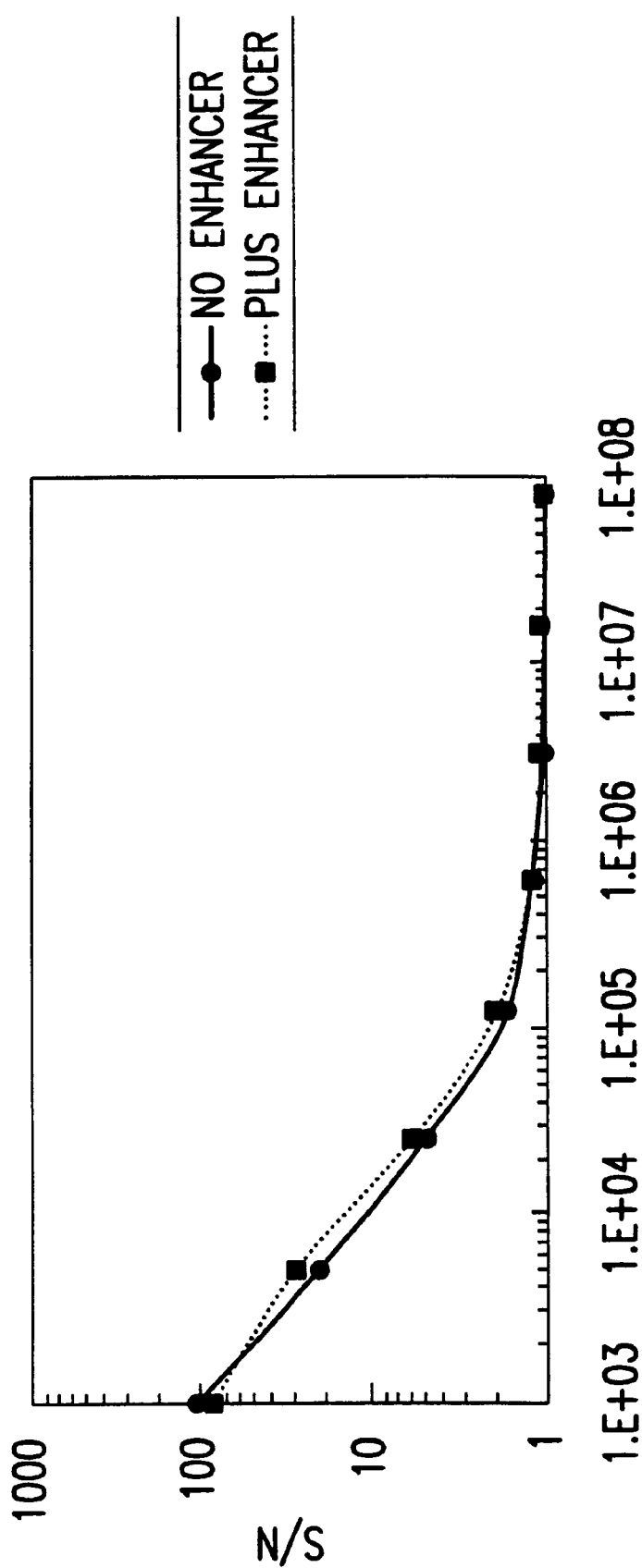
FIG. 16C is a graph showing signal to noise ratio (S/N) as a function of sialidase dilution for a substrate according to the invention with and without a quaternary polymeric onium enhancer.

A two step assay was conducted with the Oxford X-501 neuraminidase enzyme in both the presence and absence of a quaternary onium polymeric enhancer. The results and conditions are summarized in Table F and depicted graphically in FIGS. 16A–16C.

TABLE F

| | | No enhancer | | Plus Enhancer | |
|---|---|---|---|---|---|
| Sialidase, units/well | Sialidase dilution | Average RLU | S/N | Average RLU | S/N |
| 3.33E-05 | 1000 | 8785.00 | 106.06 | 527184.00 | 91.42 |
| 6.67E-06 | 5000 | 1701.67 | 20.54 | 163132.33 | 28.29 |
| 1.33E-06 | 25000 | 421.00 | 5.08 | 34451.00 | 5.97 |
| 2.67E-07 | 125000 | 144.00 | 1.74 | 11151.33 | 1.93 |
| 5.33E-08 | 625000 | 99.00 | 1.20 | 6414.33 | 1.11 |
| 1.07E-08 | 3125000 | 84.33 | 1.02 | 6021.33 | 1.04 |
| 2.13E-09 | 15625000 | 81.00 | 0.96 | 5839.33 | 1.01 |
| 4.27E-10 | 78125000 | 85.33 | 1.03 | 5811.00 | 1.01 |
| 8.53E-11 | 390625000 | 81.00 | 0.96 | 5742.00 | 1.00 |
| 1.71E-11 | 1953125000 | 80.33 | 0.97 | 5689.00 | 0.99 |
| | | 82.83 | | 5766.83 | |

The invention of this application is described above both generically and with regard to specific embodiments. A wide variety of alternatives known to those of ordinary skill in the art can be selected within the generic disclosure, and examples are not to be interpreted as limiting, unless specifically so indicated. In particular, variations of the identity of the dioxetane, buffer compositions, signal detecting apparatus, protocol time, temperatures, and conditions and the like will occur to those of ordinary skill in the art. These variations are intended to remain within the scope of the invention. The invention is not otherwise limited, except for the recitation of the claims set forth below.

What is claimed is:

1. An enzymatically cleavable chemiluminescent 1,2-dioxetane of formula I:

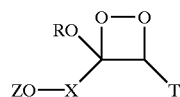

which is capable of producing light energy when decomposed;

wherein T is a substituted or unsubstituted polycycloalkyl group bonded to the 4-membered ring portion of said dioxetane by a Spiro linkage;

wherein X is an aryl or heteroaryl moiety of 6–30 carbon atoms which induces chemiluminescent decomposition of said 1,2-dioxetane upon enzymatic cleavage of said moiety Z;

wherein Z is an enzymatically cleavable group of formula II:

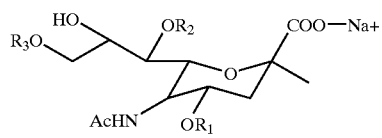

wherein $R_1$–$R_3$ are each independently H or an alkyl (branched or straight chain) of 1–4 carbon atoms, and wherein R is an alkyl, aryl, aralkyl or cycloalkyl of 1–20 carbon atoms.

2. The dioxetane of claim 1, wherein said substituted polycycloalkyl group is substituted with a member selected from the group consisting of a hydroxyl group, fluorine, chlorine, an unsubstituted straight or branched chain alkyl group of 1–6 carbon atoms, a 1–6 carbon alkyl group mono-, di- or tri- substituted with a hydroxy or 1–3 halogen atoms, a phenyl group, a cyano group and an amide group.

3. The dioxetane of claim 1, wherein said moiety X is substituted with 1–3 electron active substituents independently selected from the group consisting of halogen, chlorine, non-chloro alkoxy, aryloxy, trialkylammonium, alkylamido, arylamido, arylcarbamoyl, alkylcarbamoyl, cyano, nitro, ester, alkylsulfonamido, arylsulfonamido, triphorylmethyl, aryl, alkyl, trialkyl, triarylsilyl, alkylarylsilyl, alkylamidosulfonyl, arylarnidosulfonyl, alkylsulfonyl, arylsulfonyl, alkylthioether and arylthioether.

4. The dioxetane of claim 3, wherein each alkyl or aryl moiety comprises 1–12 carbon atoms.

5. The dioxetane of claim 1, wherein R comprises an alkyl, aryl, aralkyl or cycloalkyl containing 1–2 hetero atoms selected from the group consisting of phosphorus, nitrogen, sulfur and oxygen.

6. The dioxetane of claim 1, wherein R contains at least one halogen substituent.

7. A method of detecting the presence of neuraminidase in a sample, comprising:

combining the enzymatically cleavable chemiluminescent 1,2-dioxetane of claim 1, with said sample to form a reaction mixture, incubating said reaction mixture for a period of time sufficient to ensure cleavage of said moiety Z by any neuraminidase present in said sample; and detecting any luminescence generated as a result of said combination step;

wherein luminescence is indicative of the presence of neuraminidase.

8. The method of claim 7, wherein said reaction mixture further comprises an chemiluminescence enhancer compound.

9. The method of claim 7, wherein a base is added to said reaction mixture prior to said step of detecting luminescence.

10. The method of claim 8, wherein said enhancer is a water soluble onium polymeric salt.

11. The method of claim 9, wherein said base is added to promote luminescence.

12. The method of claim 7 wherein said luminescence is measured in a luminometer.

13. The method of claim 7 wherein the intensity of luminescence is indicative of the amount of neuraminidase in said sample.

14. An assay for detecting the presence of neuraminidase in a sample, comprising:

reacting said enzymatically cleavable chemiluminescent 1,2-dioxetane of claim 1 with a sample in an aqueous solution to form a reaction mixture;

incubating said reaction mixture;

monitoring said reaction mixture in the presence of a base and an enhancer compound to determine if light is released;

wherein the release of light is indicative of the presence and/or amount of neuraminidase in said sample.

15. The assay of claim 14, wherein said light is measured in a luminometer.

16. A kit for detecting neuraminidase in a sample, comprising:

(1) the enzymatically cleavable chemiluminescent 1,2-dioxetane compound of claim 1; and (2) a buffer solution which maintains a mixture of said 1,2-dioxetane compound and said sample at a pH of about 5.5–7.8.

17. The kit of claim 16, wherein said kit comprises a chemiluminescence enhancer compound.

18. The kit of claim 16, wherein said kit further comprises base which raises pH of a mixture of said sample and said dioxetane, after incubation of said mixture, to a value consistent with chemiluminescence of said dioxetane upon decomposition following cleavage of said moiety Z.

19. The compound of claim 1, wherein R bears at least one group which enhances the solubility of the dioxetane in aqueous preparations.

20. The compound of claim 19, wherein R bears two groups which enhance the solubility of the dioxetane reagent in aqueous preparations.

21. The compound of claim 19, wherein R bears two carboxylic acid moieties.

* * * * *